US011607435B2

(12) United States Patent
Zhao et al.

(10) Patent No.: US 11,607,435 B2
(45) Date of Patent: Mar. 21, 2023

(54) PROBIOTICS *BIFIDOBACTERIA* STRAINS

(71) Applicant: PERFECT (CHINA) CO., LTD., Guangdong (CN)

(72) Inventors: Liping Zhao, Shanghai (CN); Guojun Wu, Shanghai (CN); Menghui Zhang, Shanghai (CN); Chenhong Zhang, Shanghai (CN); Huan Wu, Shanghai (CN)

(73) Assignee: PERFECT (CHINA) CO., LTD., Guangdong (CN)

( * ) Notice: Subject to any disclaimer, the term of this patent is extended or adjusted under 35 U.S.C. 154(b) by 160 days.

(21) Appl. No.: 16/467,934

(22) PCT Filed: Feb. 10, 2017

(86) PCT No.: PCT/CN2017/073209
§ 371 (c)(1),
(2) Date: Jun. 7, 2019

(87) PCT Pub. No.: WO2018/145294
PCT Pub. Date: Aug. 16, 2018

(65) Prior Publication Data
US 2020/0069746 A1 Mar. 5, 2020

(51) Int. Cl.
*A01N 63/00* (2020.01)
*A61K 35/747* (2015.01)
*A61P 3/04* (2006.01)
*A61K 35/00* (2006.01)

(52) U.S. Cl.
CPC .............. *A61K 35/747* (2013.01); *A61P 3/04* (2018.01); *A61K 2035/115* (2013.01)

(58) Field of Classification Search
None
See application file for complete search history.

(56) References Cited

U.S. PATENT DOCUMENTS

| 2002/0037577 | A1 | 3/2002 | Park et al. | |
| 2014/0369965 | A1* | 12/2014 | Herranz | A61K 35/745 424/93.4 |
| 2018/0177833 | A1* | 6/2018 | Zhao | C12N 1/20 |

FOREIGN PATENT DOCUMENTS

| CN | 106148230 A | 11/2016 | |
| JP | 2014505467 A | 3/2014 | |
| WO | 02/38165 A1 | 5/2002 | |
| WO | 2006013588 A1 | 2/2006 | |
| WO | 2007/043933 A1 | 4/2007 | |
| WO | 2008/016214 A1 | 2/2008 | |
| WO | 2009/004076 A2 | 1/2009 | |
| WO | 2009/021824 A1 | 2/2009 | |
| WO | 2009/024429 A2 | 2/2009 | |
| WO | 2017000249 A1 | 1/2017 | |
| WO | WO-2017000249 A1 * | 1/2017 | ............... C12N 1/20 |

OTHER PUBLICATIONS

Schmieder R, et al., 2011. Quality control and preprocessing of metagenomic datasets. Bioinformatics 27:863-864.
Langmead B, et al., 2012. Fast gapped-read alignment with Bowtie 2. Nat Methods 9:357-359.
Segata N, et al., 2012. Metagenomic microbial community profiling using unique clade-specific marker genes. Nat Methods 9:811-814.
Chin CS, et al., 2013. Nonhybrid, finished microbial genome assemblies from long-read SMRT sequencing data. Nat Methods 10:563-569.
Sommer DO, et al., 2007. Minimus: a fast, lightweight genome assembler. BMC Bioinformatics 8:64.
Hyatt D, et al., 2010. Prodigal: prokaryotic gene recognition and translation initiation site identification. BMC Bioinformatics 11:119.
Lagesen K, et al., 2007. RNAmmer: consistent and rapid annotation of ribosomal RNA genes. Nucleic Acids Res 35:3100-3108.
Lowe TM, et al., 1997. tRNAscan-SE: a program for improved detection of transfer RNA genes in genomic sequence. Nucleic Acids Res 25:955-964.
Edgar RC., 2010. Search and clustering orders of magnitude faster than BLAST. Bioinformatics 26:2460-2461.
Zhao Y, et al., 2012. PGAP: pan-genomes analysis pipeline. Bioinformatics 28:416-418.
Kurtz S, et al., 2004. Versatile and open software for comparing large genomes. Genome Biol 5:R12.
Yin Y, et al., 2012. dbCAN: a web resouice for automated carbohydrate-active enzyme annotation. Nucleic Acids Res 40:W445-451.
Finn RD, et al., 2011. HMMER web server: interactive sequence similarity searching. Nucleic Acids Res 39:W29-37.
Extended European Search Report from counterpart EP17895623.1, dated Jan. 10, 2020.
Vietnam Office Action from counterpart VN1201904412, dated Oct. 8, 2019.
Taiwanese Office Action from counterpart TW107104756, dated Oct. 29, 2019.
Lee et al., J. Appl. Microbiol. 2007, vol. 103, pp. 1140-1146.
Li et al., Hepatology, 2003, 37(2), pp. 343-350.
International Search Report and Written Opinion, dated Nov. 16, 2017, issued in corresponding International Application No. PCT/CN2017/073209, 9 pages.
Zhao L., 2013, The gut microbiota and obesity: from correlation to causality. Nat Rev Microbiol 11:639-647.
Boulange CL, et al., 2016. Impact of the gut microbiota on inflammation, obesity, and metabolic disease. Genome Med 8:42.
Qin N, et al., 2014. Alterations of the human gut microbiome in liver cirrhosis. Nature 513:59-64.
Zhang X, et al., 2015. The oral and gut microbiomes are perturbed in rheumatoid arthritis and partly normalized after treatment. Nat Med 21:895-905.
Xu J, et al., 2015. Structural modulation of gut microbiota during alleviation of type 2 diabetes with a Chinese herbal formula. ISME J 9:552-562.

(Continued)

*Primary Examiner* — Jana A Hines
*Assistant Examiner* — Khatol S Shahnan Shah
(74) *Attorney, Agent, or Firm* — Oliff PLC

(57) ABSTRACT

This invention relates to novel probiotic Bifidobacteria strains, particularly, *B. pseudocatenulatum* strains, and their use as probiotic, and food products, feed products, dietary supplements and pharmaceutical formulations containing them. The bacteria are suitable for the treatment of obesity, diabetes, and related conditions.

9 Claims, 11 Drawing Sheets

(56) References Cited

OTHER PUBLICATIONS

Kelly CR, et al., 2015. Update on Fecal Microbiota Transplantation 2015: Indications, Methodologies, Mechanisms, and Outlook. Gastroenterology 149:223-237.
Xiao S., et al., 2014. A gut microbiota-targeted dietary intervention for amelioration of chronic inflammation underlying metabolic syndrome. FEMS Microbiol Ecol 87:357-367.
Human Microbiome Project C. 2012. Structure, function and diversity of the healthy human microbiome. Nature 486:207-214.
Zhang C, et al., 2015. Dietary Modulation of Gut Microbiota Contributes to Alleviation of Both Genetic and Simple Obesity in Children. EBioMedicine 2:966-982.
Wu H, et al., 2015. Exploring Carbohydrate Utilization Capacity of Bifidobacterium pseudocate.
Nulatum Isolated from a Morbidly Obese Child after Dietary Intervention. Genomics and Applied Biology 34:1384-1391.
Grimm V, et al., 2014. Bifidobacteria-host interactions—an update on colonisation factors. Biomed Res Int 2014:960826.
Labruna G, et al., 2011. High leptin/adiponectin ratio and serum triglycerides are associated with an "at-risk" phenotype in young severely obese patients. Obesity (Silver Spring) 19:1492-1496.
Zweigner J, et al., 2006. The role of lipopolysaccharide-binding protein in modulating the innate immune response. Microbes Infect 8:946-952.
Arumugam M, et al., 2011. Enterotypes of the human gut microbiome. Nature 473:174-180.
Fujimoto T, et al., 2013. Decreased abundance of Faecalibacterium prausnitzii in the gut microbiota of Crohn's disease. J Gastroenterol Hepatol 28:613-619.
Sokol H, et al., 2008. Faecalibacterium prausnitzii is an anti-inflammatory commensal bacterium identified by gut microbiota analysis of Crohn disease patients. Proc Natl Acad Sci U S A 105:16731-16736.
Ganzle MG, et al., 2012. Metabolism of oligosaccharides and starch in lactobacilli: a. review. Front Microbiol 3:340.
Andreasen AS, et al., 2010. Effects of Lactobacillus acidophilus NCFM on insulin sensitivity and the systemic inflammatory response in human subjects. Br J Nutr 104:1831-1838.
Hulston CJ, et al., 2015. Probiotic supplementation prevents high-fat, overfeeding-induced insulin resistance in human subjects. Br J Nutr 113:596-602.
Charbonneau MR, et al., 2016. A microbial perspective of human developmental biology. Nature 535:48-55.
Wang J, et al., 2015. Modulation of gut microbiota during probiotic-mediated attenuation of metabolic syndrome in high fat diet-fed mice. ISME J 9:1-15.
Stenman LK, et al., 2014. Potential probiotic Bifidobacterium animalis ssp. lactis 420 prevents weight gain and glucose intolerance in diet-induced obese mice. Benef Microbes 5:437-445.
Staley J, et al., 1984. Classification of prokaryotes organisms: an overview. Krieg, NR, Holt, JG Bergey's manual of systematic bacteriology 1.
Ahn TH, et al., 2015. Sigma: strain-level inference of genomes from metagenomic analysis for biosurveillance. Bioinformatics 31:170-177.
Morita H, et al., 2015. Complete genome sequence of Bifidobacterium pseudocatenulatum JCM 1200(T) isolated from infant feces. J. Biotechnol 210:68-69.
Bottacini F, et al., 2010. Comparative genomics of the genus Bifidobacterium. Microbiology 156:3243-3254.
Galperin MY, et al., 2015. Expanded microbial genome coverage and improved protein family annotation in the COG database. Nucleic Acids Res 43:D261-269.
Bottacini F, et al., 2014. Comparative genomics of the Bifidobacterium breve taxon. BMC Genomics 15:170.
O'Callaghan A, et al., 2015. Pangenome analysis of Bifidobacterium longum and site-directed mutagenesis through by-pass of restriction-modification systems. BMC Genomics 16:832.
Begley M, et al., 2005. The interaction between bacteria and bile. Ferns Microbiology Reviews 29:625-651.
Candela M, et al. 2009. Bifidobacterial enolase, a cell surface receptor for human plasminogen involved in the interaction with the host. Microbiology 155:3294-3303.
Candela M, et al., 2010. DnaK from Bifidobacterium animalis subsp. lactis is a surface-exposed human plasminogen receptor upregulated in response to bile salts. Microbiology 156:1609-1618.
Gonzalez-Rodriguez I, et al., 2012. Role of extracellular transaldolase from Bifidobacterium bifidum in mucin adhesion and aggregation. Appl Environ Microbiol 78:3992-3998.
Pareti FI, et al., 1986. Isolation and characterization of a collagen binding domain in human von Willebrand factor. J Biol Chem 261:15310-15315.
Richter M, et al., 2009. Shifting the genomic gold standard for the prokaryotic species definition. Proc Natl Acad Sci USA 106:19126-19131.
Schmid J, et al., 2015. Bacterial exopolysaccharides: biosynthesis pathways and engineering strategies. Front Microbiol 6:496.
Hidalgo-Cantabrana C, et al., 2014. Genomic overview and biological functions of exopolysaccharide biosynthesis in Bifidobacterium spp. Appl Environ Microbiol 80:9-18.
Zhang XL, et al., 2004. Microdiversity of phenol hydroxylase genes among phenol-degrading isolates of Alcaligenes sp from an activated sludge system. Fems Microbiology Letters 237:369-375.
Mao YJ, et al., 2010. Versatile aromatic compound-degrading capacity and microdiversity of Thauera strains isolated from a coking wastewater treatment bioreactor. Journal of Industrial Microbiology & Biotechnology 37:927-934.
Patra R, et al., 2012. Multiple Infection and Microdiversity among Helicobacter pylori Isolates in a Single Host in India. Plos One 7.
Biely P. 2012. Microbial carbohydrate esterases deacetylating plant polysaccharides. Biotechnol Adv 30:1575-1588.
Jezbera J,et al., 2013. Patterns of Limnohabitans microdiversity across a large set of freshwater habitats as revealed by Reverse Line Blot Hybridization. PLoS One 8:e58527.
Moore LR, et al., 1998. Physiology and molecular phylogeny of coexisting Prochlorococcus ecotypes. Nature 393:464-467.
Zhang C, et al., 2016. Strain-level dissection of the contribution of the gut microbiome to human metabolic disease. Genome Med 8:41.
Fei N, et al., 2013. An opportunistic pathogen isolated from the gut of an obese human causes obesity in germfree mice. ISME J 7:880-884.
Dodt M, et al., 2012. FLEXBAR-Flexible Barcode and Adapter Processing for Next-Generation Sequencing Platforms. Biology (Basel) 1:895-905.
Chenhong Zhang et al., "Dietary Modulation of Gut Microbiota Contributes to Alleviation of Both Genetic and Simple Obesity in Children", EBioMedicine (2015), vol. 2, pp. 968-984, Table S9.
Japanese Office Action regarding corresponding application No. JP2019-543235, dated Dec. 23, 2020.

* cited by examiner

Figure 7    The bioclincial parameters changed during the intervention. (red) Anthropometric markers. (green) Plasma lipid homeostasis. (blue) Plasma glucose homeostasis. (purple) Inflammation related markers. SAA: serum amyloid A protein; CRP: C-reactive protein Figure 8  The abundance of the 9 identified *Bifidobacterium* species in the gut microbial community on Day 105.

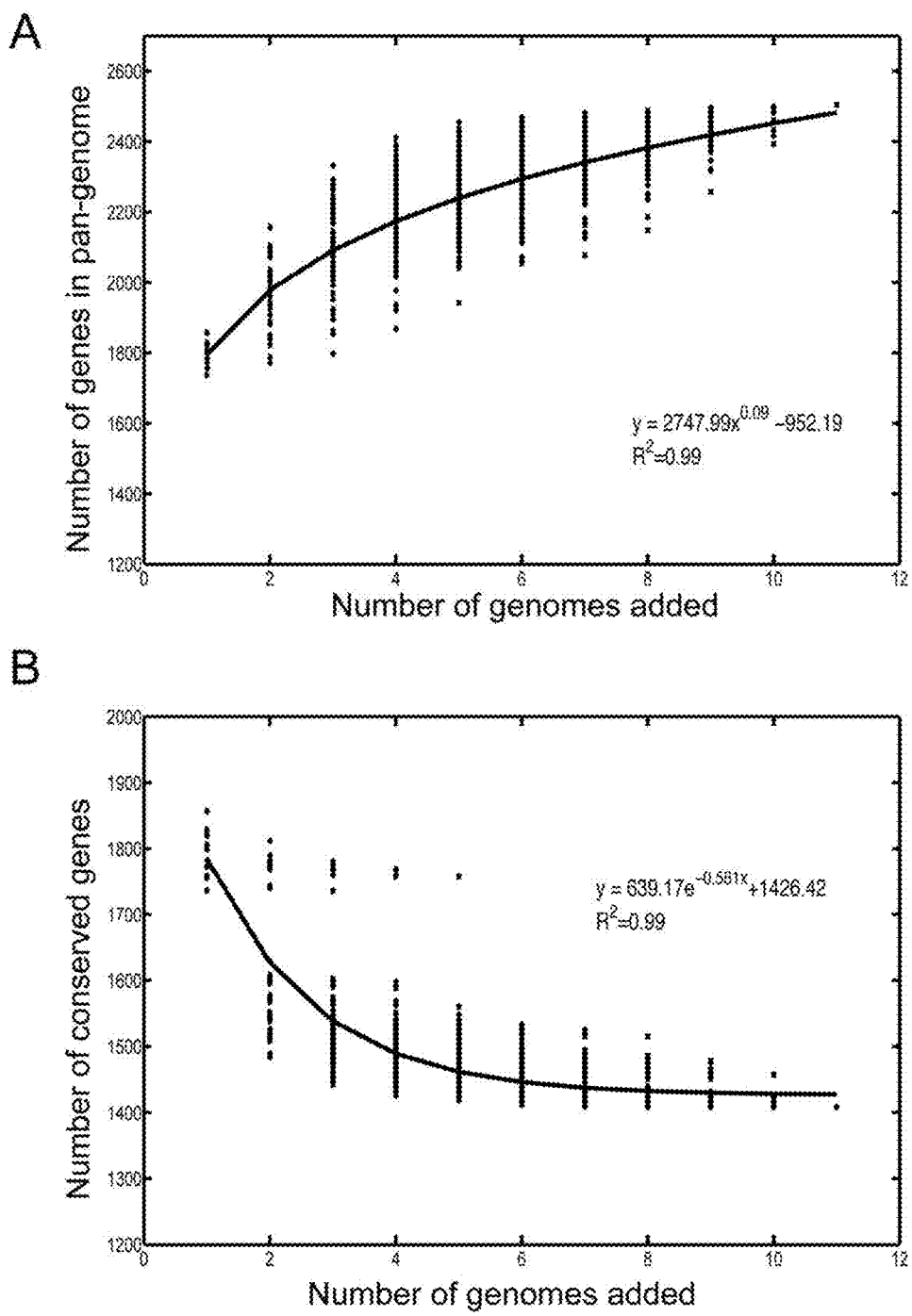

Fig. 9

Figure 9　　Pan-genome and core-genome curve of B.pseudocatenulatum. (A) Accumulated number of genes in the B.pseudocatenulatum pan-genome plotted against the number of genomes added. The deduced mathematical function is also indicated. (B) The cumulative decreased number of genes attributed to the core-genome plotted against the number of added genomes. The deduced mathematical function is also reported Figure 10    Physical maps of the predicted *eps* clusters from the six complete *B.pseudocatenulatum*. The genes were showed as colored arrows according to their potential functions.

Figure 11  Distribution of dispensable and unique COGs in the six *B.pseudocatenulatum* genomes. The heatmap shows the copy number of genes annotated as the particular COG function. The strains are clustered with Jaccard distance and Ward linkage method.

PROBIOTICS *BIFIDOBACTERIA* STRAINS

This application is a National Stage of PCT/CN2017/073209, filed Feb. 10, 2017, which is incorporated herein by reference in its entirety.

FIELD OF THE INVENTION

This invention relates to novel Bifidobacteria strains and their uses, to food products, feed products, dietary supplements and pharmaceutical formulations containing them, and to methods of making and using these compositions.

BACKGROUND OF THE INVENTION

Probiotics, generally understood to mean "live microorganisms that when administered in adequate amounts confer a health benefit on the host," have been used widely for the prevention and treatment of a wide range of diseases, and there is strong evidence for their efficacy in some clinical scenarios. For example, WO 2007/043933 describes the use of probiotic bacteria for the manufacture of food and feed products, dietary supplements, for controlling weight gain, preventing obesity, increasing satiety, prolonging satiation, reducing food intake, reducing fat deposition, improving energy metabolism, enhancing insulin sensitivity, treating obesity and treating insulin insensitivity.

WO 2009/024429 describes the use of a primary composition comprising an agent that reduces the amount of proteobacteria, in particular enterobacteria and/or deferribacteres in the gut for the treatment or prevention of metabolic disorders, to support and/or to support weight management.

WO 2009/004076 describes the use of probiotic bacteria for normalising plasma glucose concentrations, improving insulin sensitivity, and reducing the risk of development in pregnant women, and preventing gestational diabetes.

WO 2009/021824 describes the use of probiotic bacteria, in particular *Lactobacillus rhamnosus*, to treat obesity, treat metabolic disorders, and support weight loss and/or weight maintenance.

WO 2008/016214 describes a probiotic lactic acid bacterium of the strain *Lactobacillus gasseri* BNR17 and its use in the inhibition of weight gain.

WO 02/38165 describes use of a strain of *Lactobacillus* (in particular, *Lactobacillus plantarum*) in reducing the risk factors involved in the metabolic syndrome.

US 2002/0037577 describes the use of microorganisms, such as *Lactobacilli*, for the treatment or prevention of obesity or diabetes mellitus by reduction of the amount of monosaccharide or disaccharide which may be absorbed into the body, by converting such compounds into polymeric materials which cannot be absorbed by the intestine.

Lee et al., J. Appl. Microbiol. 2007, 103, 1140-1146, describes the anti-obesity activity of trans-10, cis-12-conjugated linoleic acid (CLA)-producing bacterium of the strain *Lactobacillus plantarum* PL62 in mice.

Li et al., Hepatology, 2003, 37(2), 343-350, describe the use of probiotics and anti-TNF antibodies in a mouse model for non-alcoholic fatty liver disease.

US2014/0369965 discloses a *Bifidobacterium pseudocatenulatum* strain isolated from the feces of healthy breast-feeding mice. The same document further discloses the use of this strain, along with its cell components, metabolites, and secreted molecules, and combinations thereof with other microorganisms for the prevention and/or treatment of obesity, overweight, hyperglycemia and diabetes, hepatic steatosis or fatty liver, dyslipidemia, metabolic syndrome, immune system dysfunction associated with obesity and overweight; and an unbalanced composition of the intestinal microbiota associated with obesity and overweight. However, this strain is not derived from humans.

PCT/CN2015/082887 discloses strains of *Bifidobacterium pseudocatenulatum* found to be abundant in fecal samples of individuals subjected to hospitalized intervention with an established diet based on whole-grains, traditional Chinese medicinal foods and prebiotics (WTP diet). These individuals, after the intervention, have shown a significant alleviation of the metabolic deteriorations in children with both genetic and simple obesity after 30 days of the dietary intervention. However, these strains, though found to be abundant in those post-intervention individuals, were not established to have significantly increased by the intervention, or to be responsible for the patients' improved health conditions.

In other words, existing probiotics have many limitations, and there is a need for new strains of probiotic microorganisms.

SUMMARY OF THE INVENTION

The genomic bases of the response to dietary intervention of human gut beneficial bacteria remains elusive, which hinders the precision manipulation of the microbiota for human health. After receiving a dietary intervention enriched with non-digestible carbohydrates for 105 days, a genetically obese child with Prader-Willi Syndrome lost 18.4% of his body weight and showed significant improvement in his bioclinical parameters. Five isolates (termed PERFECT-2017-0001 with accession no. CGMCC 13650, PERFECT-2017-0002 with accession no. CGMCC 13651 PERFECT-2017-0003 with accession no. CGMCC 13653, PERFECT-2017-0004 with accession no. CGMCC 13654 and C95) of one of the most abundantly promoted species, *Bifidobacterium pseudocatenulatum*, were obtained from a post-intervention fecal sample. Intriguingly, these five *B. pseudocatenulatum* strains showed differential responses during the intervention. Two strains were almost unaffected, while the other three were promoted to different extents by the changes in dietary carbohydrate resources. The differential responses of these strains were consistent with their functional clustering based on the COG (Cluster of Orthologous Group), including those involved with the ABC-type sugar transport systems, suggesting that the strain-specific genomic variations may have contributed to the niche adaptation. Particularly, *B. pseudocatenulatum* PERFECT-2017-0002, which had the most diverse types and highest gene copy numbers of carbohydrate-active enzymes targeting plant polysaccharides, had the highest abundance after the intervention.

Accordingly, in one aspect, the invention provides the use of a bacterium of the genus *Bifidobacterium* or a mixture thereof in the manufacture of a food product, dietary supplement or medicament for treating obesity, controlling weight gain and/or inducing weight loss in a mammal.

In another aspect, the invention discloses a composition comprising (1) a *Bifidobacterium pseudocatenulatum* strain PERFECT-2017-0001 or PERFECT-2017-0002, or a highly similar strain, or (2) a strain derived therefrom; (3) a pharmaceutically acceptable or dietary carrier.

In another aspect, the invention discloses a method for preparing the composition of the present invention, comprising formulating the *Bifidobacterium pseudocatenulatum* strain PERFECT-2017-0001 or PERFECT-2017-0002, or the highly similar strain into a suitable composition.

In another aspect, the invention discloses a method for the prevention and/or treatment of a disease selected from the group consisting of overweight, obesity, hyperglycemia, diabetes, fatty liver, dyslipidemia, metabolic syndrome, infections in obese or overweight subjects and/or adipocyte hypertrophy said method comprising the administration of the composition of the present invention to a subject in need thereof.

In another aspect, the invention discloses a method for reducing simple or genetic obesity, alleviating metabolic deteriorations, or reducing inflammation and fat accumulation in a subject in need thereof, comprising the administration of the composition of the present invention to a subject in need thereof.

In another aspect, the invention discloses a method for establishing as foundation species that define the structure of a healthy gut ecosystem, rendering a gut environment unfavorable to pathogenic and detrimental bacteria, reducing the concentration of enterobacteria in intestinal content with respect to an untreated control, the method comprising the administration of the composition of the present invention to a subject in need thereof.

In another aspect, the invention discloses a method for treating diabetes in a subject in need thereof, comprising the administration of the composition of the present invention to a subject in need thereof.

BRIEF DESCRIPTION OF THE DRAWINGS

FIG. 9 Pan-genome and core-genome curve of *B. pseudocatenulatum*. (A) Accumulated number of genes in the *B. pseudocatenulatum* pan-genome plotted against the number of genomes added. The deduced mathematical function is also indicated. (B) The cumulative decreased number of genes attributed to the core-genome plotted against the number of added genomes. The deduced mathematical function is also reported.

DETAILED DESCRIPTION OF THE INVENTION

Figure 1:
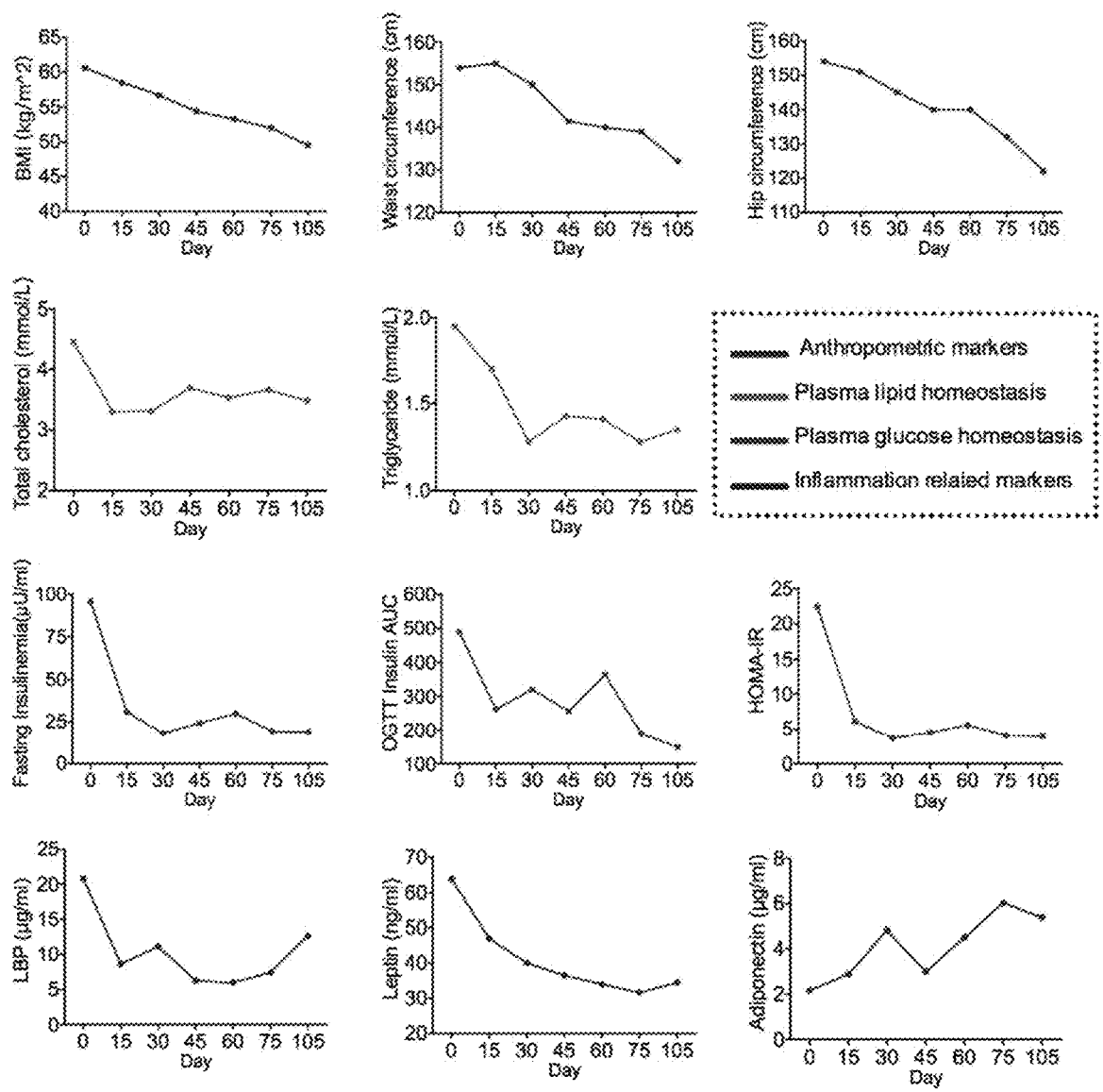
FIG. 1 shows improved bioclinical parameters and inflammatory conditions after the intervention. (red) Anthropometric markers. (green) Plasma lipid homeostasis. (blue) Plasma glucose homeostasis. (purple) Inflammation-related markers. BMI: body mass index; OGTT: Oral glucose tolerance test; LBP: Lipopolysaccharide-binding protein.

The present inventors have discovered strains of *B. pseudocatenulatum* that can reduce simple or genetic obesity, alleviate metabolic deteriorations, and reduce inflammation and fat accumulation in mammals. The *B. pseudocatenulatum* strains of the present invention, alone or in combination with other probiotic microorganisms, when established in the gut, function as foundation species that define the structure of a healthy gut ecosystem, for example by rendering the gut environment unfavorable to pathogenic and detrimental bacteria, possibly via increased production of acetate.

As described in more details below, the *B. pseudocatenulatum* strains of the present invention were isolated from individuals subjected to hospitalized intervention with a previous published diet based on whole-grains, traditional Chinese medicinal foods and prebiotics (WTP diet) (S. Xiao et al., A gut microbiota-targeted dietary intervention for amelioration of chronic inflammation underlying metabolic syndrome. *FEMS Microbiol Eco/87*, 357 (February 2014). These individuals, after the intervention, have shown a significant alleviation of the metabolic deteriorations in children with both genetic and simple obesity after 30 days of the dietary intervention.

As detailed in the Examples below, the present inventors, successfully obtained a large number of strains of the foundation species of the present invention, identified as *B. pseudocatenulatum*. Representative isolates are the PERFECT-2017-0001 and PERFECT-2017-0002 strains, deposited in the China General Microbiological Culture Collection Center (CGMCC) on Jan. 23, 2017, with the accession nos. of CGMCC 13650 and CGMCC 13651 respectively.

The probiotic strains of the present invention can be cultured, maintained and propagated using established methods well-known to those ordinarily skilled in the art, some of which methods are exemplified in the Examples below.

The bacterium used in the present invention is a *Bifidobacterium pseudocatenulatum* strain or a mixture thereof.

Preferably the *Bifidobacterium* to be used in the present invention is a *B. pseudocatenulatum* PERFECT-2017-0001 or PERFECT-2017-0002 strain.

The bacterium may be used in any form capable of exerting the effects described herein. Preferably, the bacteria are viable bacteria.

The bacteria may comprise whole bacteria or may comprise bacterial components. Examples of such components include bacterial cell wall components such as peptidoglycan, bacterial nucleic acids such as DNA and RNA, bacterial membrane components, and bacterial structural components such as proteins, carbohydrates, lipids and combinations of these such as lipoproteins, glycolipids and glycoproteins.

The bacteria may also or alternatively comprise bacterial metabolites. In this specification the term 'bacterial metabolites' includes all molecules produced or modified by the (probiotic) bacteria as a result of bacterial metabolism during growth, survival, persistence, transit or existence of bacteria during probiotic product manufacture and storage and during gastrointestinal transit in a mammal. Examples include all organic acids, inorganic acids, bases, proteins and peptides, enzymes and co-enzymes, amino acids and nucleic acids, carbohydrates, lipids, glycoproteins, lipoproteins, glycolipids, vitamins, all bioactive compounds, metabolites containing an inorganic component, and all small molecules, for example nitrous molecules or molecules containing a sulphurous acid. Preferably the bacteria comprise whole bacteria, more preferably whole viable bacteria.

Preferably, the *Bifidobacterium* used in accordance with the present invention is one which is suitable for human and/or animal consumption. In the present invention, the *Bifidobacterium* used may be of the same type (species and strain) or may comprise a mixture of species and/or strains.

Suitable Bifidobacteria are selected from the species *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*, and combinations of any thereof.

As shown in the Examples below, *Lactobacillus mucosae*, especially those that are highly similar to *L. mucosae* strain 32, were highly increased post diet intervention. Thus, one preferred bacterium for use in combination with a *B. pseudocatenulatum* strain of the present invention is *L. mucosae*, especially Strain 32.

In one embodiment, the bacterium used in the present invention is a probiotic bacterium. In this specification the term 'probiotic bacterium' is defined as covering any non-pathogenic bacterium which, when administered live in adequate amounts, confer a health benefit on the host. These probiotic strains generally have the ability to survive the passage through the upper part of the digestive tract. They are non-pathogenic, non-toxic and exercise their beneficial effect on health on the one hand via ecological interactions with the resident flora in the digestive tract, and on the other hand via their ability to influence the immune system in a positive manner via the "GALT" (gut-associated lymphoid tissue). Depending on the definition of probiotics, these bacteria, when given in a sufficient number, have the ability to progress live through the intestine, however they do not cross the intestinal barrier and their primary effects are therefore induced in the lumen and/or the wall of the gastrointestinal tract. They then form part of the resident flora during the administration period. This colonization (or transient colonization) allows the probiotic bacteria to exercise a beneficial effect, such as the repression of potentially pathogenic micro-organisms present in the flora and interactions with the immune system of the intestine.

In some embodiments, the *Bifidobacterium* is used in the present invention together with a bacterium of the genus *Lactobacillus*. A combination of *Bifidobacterium* and *Lactobacillus* bacteria according to the present invention exhibits a synergistic effect in certain applications (i.e. an effect which is greater than the additive effect of the bacteria when used separately). For example, combinations which, in addition to having effect on the mammal as single components, may have beneficial effect on the other components of the combination, for example by producing metabolites which are then in turn used as an energy source by other components of the combination, or maintaining physiological conditions which favour the other components.

Typically, the *Lactobacillus* bacteria are selected from the species *Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus crispatus, Lactobacillus gassed, Lactobacillus johnsonii* and *Lactobacillus jensenii*, and combinations of any thereof.

In preferred embodiments, the *Lactobacillus* bacterium used in the present invention is a probiotic *Lactobacillus*. Preferably, the *Lactobacillus* bacterium used in the present invention of the species *Lactobacillus acidophilus*.

Dosage and Administration. Administration of probiotic bacteria can be accomplished by any method likely to introduce the organisms into the digestive tract. The bacteria can be mixed with a carrier and applied to liquid or solid feed or to drinking water. The carrier material should be non-toxic to the bacteria and the animal. Preferably, the carrier contains an ingredient that promotes viability of the bacteria during storage. The bacteria can also be formulated as an inoculant paste to be directly injected into an animal's mouth. The formulation can include added ingredients to improve palatability, improve shelf-life, impart nutritional benefits, and the like. If a reproducible and measured dose is desired, the bacteria can be administered by a rumen cannula. The amount of probiotic bacteria to be administered is governed by factors affecting efficacy. When administered in feed or drinking water the dosage can be spread over a period of days or even weeks. The cumulative effect of lower doses administered over several days can be greater than a single larger dose thereof. By monitoring the numbers of *Salmonella* strains that cause human salmonellosis in feces before, during and after administration of dominant probiotic bacteria, those skilled in the art can readily ascertain the dosage level needed to reduce the amount of *Salmonella* strains that cause human salmonellosis carried by the animals. One or more strains of dominant probiotic bacteria can be administered together. A combination of strains can be advantageous because individual animals may differ as to the strain which is most persistent in a given individual.

The *Bifidobacterium pseudocatenulatum* used in accordance with the present invention may comprise from $10^6$ to $10^{12}$ CFU of bacteria/g of support, and more particularly from $10^8$ to $10^{12}$ CFU of bacteria/g of support, preferably $10^9$ to $10^{12}$ CFU/g for the lyophilized form.

Suitably, the *B. pseudocatenulatum* may be administered at a dosage of from about $10^6$ to about $10^{12}$ CFU of microorganism/dose, preferably about $10^8$ to about $10^{12}$ CFU of microorganism/dose. By the term "per dose" it is meant that this amount of microorganism is provided to a subject either per day or per intake, preferably per day. For example, if the microorganism is to be administered in a food product (for example in a yoghurt)—then the yoghurt will preferably contain from about $10^8$ to $10^{12}$ CFU of the microorganism. Alternatively, however, this amount of microorganism may be split into multiple administrations each consisting of a smaller amount of microbial loading—so long as the overall amount of microorganism received by the subject in any specific time (for instance each 24 hour period) is from about $10^6$ to about $10^{12}$ CFU of microorganism, preferably $10^8$ to about $10^{12}$ CFU of microorganism.

In accordance with the present invention an effective amount of at least one strain of a microorganism may be at least $10^6$ CFU of microorganism/dose, preferably from about $10^6$ to about $10^{12}$ CFU of microorganism/dose, preferably about $10^8$ to about $10^{12}$ CFU of microorganism/dose.

In one embodiment, the *B. pseudocatenulatum* strain may be administered at a dosage of from about $10^6$ to about $10^{12}$ CFU of microorganism/day, preferably about $10^8$ to about $10^{12}$ CFU of microorganism/day. Hence, the effective amount in this embodiment may be from about $10^6$ to about $10^{12}$ CFU of microorganism/day, preferably about $10^8$ to about $10^{12}$ CFU of microorganism/day.

CFU stands for "colony-forming units". By 'support' is meant the food product, dietary supplement or the pharmaceutically acceptable support.

When Bifidobacteria are used in the present invention together with another probiotic bacterium, the bacteria may be present in any ratio capable of achieving the desired effects of the invention described herein.

Subjects/Medical Indications

The *B. pseudocatenulatum* strain is administered to a mammal, including for example livestock (including cattle, horses, pigs, chickens and sheep), and humans. In some aspects of the present invention the mammal is a companion animal (including pets), such as a dog or a cat for instance. In some aspects of the present invention, the subject may suitably be a human.

The *B. pseudocatenulatum* strain may be suitable for treating a number of diseases or conditions in mammals (particularly humans). In this specification the term "treatment" or "treating" refers to any administration of the *B. pseudocatenulatum* strain of the present invention in (1) preventing the specified disease from occurring in a mammal which may be predisposed to the disease but does not yet experience or display the pathology or symptomatology of the disease (including prevention of one or more risk factors associated with the disease); (2) inhibiting the disease in a mammal that is experiencing or displaying the pathology or symptomatology of the diseased, or (3) ameliorating the disease in a mammal that is experiencing or displaying the pathology or symptomatology of the diseased.

The *B. pseudocatenulatum* strain of the present invention is suitable for administration to both diabetic and obese mammals. They could also be suitable for diabetic and non-obese mammals, as well as to obese mammals possessing the risk factors for diabetes, but not yet in a diabetic state. This aspect is discussed in more detail below.

As described in more detail in the Examples below, the *B. pseudocatenulatum* strain of the present invention has a number of biological activities. In particular, the Bifidobacteria used in the present invention are capable of normalising insulin sensitivity, increasing fed insulin secretion, decreasing fasted insulin secretion, improving glucose tolerance in a mammal. These effects confer the potential for use in the treatment of diabetes and diabetes-related conditions (in particular, Type 2 diabetes and impaired glucose tolerance).

In addition, the Bifidobacteria used in the present invention are capable of inducing weight loss and lowering body fat mass (in particular, mesenteric fat mass). These effects confer the potential for use in the treatment of obesity and controlling weight gain and/or inducing weight loss in a mammal.

In particular, as described in more detail in the Examples below, the Bifidobacteria used in combination with *Lactobacillus* bacteria (particularly *Lactobacillus acidophilus* bacteria) in accordance with the present invention are capable of inducing weight loss and lowering body fat mass (in particular, mesenteric fat mass). These effects confer the potential for use in the treatment of obesity and controlling weight gain and/or inducing weight loss in a mammal.

In this specification, the term obesity is linked to body mass index (BMI). The body mass index (BMI) (calculated as weight in kilograms divided by the square of height in metres) is the most commonly accepted measurement for overweight and/or obesity. A BMI exceeding 25 is considered overweight. Obesity is defined as a BMI of 30 or more, with a BMI of 35 or more considered as serious comorbidity obesity and a BMI of 40 or more considered morbid obesity.

As noted above, the term "obesity" as used herein includes obesity, comorbidity obesity and morbid obesity. Therefore, the term "obese" as used here may be defined as a subject having a BMI of more than or equal to 30. In some embodiments, suitably an obese subject may have a BMI of more than or equal to 30, suitably 35, suitably 40.

While the composition of the invention is particularly suitable for use in patients who are both diabetic and obese, the composition is also suitable for those who are diabetic but not obese. It may also be suitable for use in obese patients possessing the risk factors for diabetes, but not yet in a diabetic state, as it could be expected that an obese person (but not diabetic), could limit the metabolic consequences of his obesity, i.e. the diabetes or at least insulino-resistance development.

In addition, the Bifidobacteria used in the present invention may be used for treating metabolic syndrome in a mammal. Metabolic syndrome is a combination of medical disorders that increase the risk of developing cardiovascular disease and diabetes. Metabolic syndrome is also known as metabolic syndrome X, syndrome X, insulin resistance syndrome, Reaven's syndrome or CHAOS (Australia).

Genetic Obesity

In further embodiments, the Bifidobacteria (and, if present, the *Lactobacilli*) used in the present invention may be used to lower tissue inflammation (particularly, although not exclusively, liver tissue inflammation, muscle tissue inflammation and/or adipose tissue inflammation) in a mammal.

Examples of cardiovascular diseases treatable by use of the Bifidobacteria (and, if present, the *Lactobacilli*) according to the present invention include aneurysm, angina, atherosclerosis, cerebrovascular accident (stroke), cerebrovascular disease, congestive heart failure (CHF), coronary artery disease, myocardial infarction (heart attack) and peripheral vascular disease.

It is envisaged within the scope of the present invention that the embodiments of the invention can be combined such that combinations of any of the features described herein are included within the scope of the present invention. In particular, it is envisaged within the scope of the present invention that any of the therapeutic effects of the bacteria may be exhibited concomitantly.

Compositions

While is it possible to administer the *B. pseudocatenulatum* strain of the present invention alone according to the present invention (i.e. without any support, diluent or excipient), the *B. pseudocatenulatum* strain of the present invention is typically and preferably administered on or in a support as part of a product, in particular as a component of a food product, a dietary supplement or a pharmaceutical formulation. These products typically contain additional components well known to those skilled in the art.

Any product which can benefit from the composition may be used in the present invention. These include but are not limited to foods, particularly fruit conserves and dairy foods and dairy food-derived products, and pharmaceutical products. The *B. pseudocatenulatum* strain of the present invention may be referred to herein as "the composition of the present invention" or "the composition".

Food

In one embodiment, the *B. pseudocatenulatum* strain of the present invention is employed in a food product such as a food supplement, a drink or a powder based on milk. Here, the term "food" is used in a broad sense and covers food for humans as well food for animals (i.e. a feed). In a preferred aspect, the food is for human consumption.

The food may be in the form of a solution or as a solid—depending on the use and/or the mode of application and/or the mode of administration. When used as, or in the preparation of a food, such as functional food, the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

The term "dairy product" as used herein is meant to include a medium comprising milk of animal and/or vegetable origin. As milk of animal origin there can be mentioned cow's, sheep's, goat's or buffalo's milk. As milk of vegetable origin there can be mentioned any fermentable substance of vegetable origin which can be used according to the invention, in particular originating from soybeans, rice or cereals.

For certain aspects, preferably the present invention may be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing the composition according to the present invention with another food ingredient.

Advantageously, the present invention relates to products that have been contacted with the composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is preferably admixed with the product. Alternatively, the composition may be included in the emulsion or raw ingredients of a foodstuff. In a further alternative, the composition may be applied as a seasoning, glaze, colorant mixture, and the like.

The compositions of the present invention may be applied to intersperse, coat and/or impregnate a product with a controlled amount of a microorganism.

Preferably, the composition is used to ferment milk or sucrose fortified milk or lactic media with sucrose and/or maltose where the resulting media containing all components of the composition—i.e. said microorganism according to the present invention—can can be added as an ingredient to yoghurt milk in suitable concentrations such as for example in concentrations in the final product which offer a daily dose of $10^6$-$10^{10}$ cfu. The microorganism according to the present invention may be used before or after fermentation of the yoghurt.

For some aspects the microorganisms according to the present invention are used as, or in the preparation of, animal feeds, such as livestock feeds, in particular poultry (such as chicken) feed, or pet food.

Advantageously, where the product is a food product, the *B. pseudocatenulatum* strain of the present invention should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognize that shelf-life times will vary upon the type of foodstuff, the size of the foodstuff, storage temperatures, processing conditions, packaging material and packaging equipment.

Food Ingredient, Food Supplements, and Functional Foods

The composition of the present invention may be used as a food ingredient and/or feed ingredient. As used herein the term "food ingredient" or "feed ingredient" includes a formulation which is or can be added to functional foods or foodstuffs as a nutritional supplement. The food ingredient may be in the form of a solution or as a solid—depending on the use and/or the mode of application and/or the mode of administration The composition of the present invention may be—or may be added to—food supplements (also referred to herein as dietary supplements).

The composition of the present invention may be—or may be added to—functional foods. As used herein, the term "functional food" means food which is capable of providing not only a nutritional effect, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect. Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Medicament

The term "medicament" as used herein encompasses medicaments for both human and animal usage in human and veterinary medicine. In addition, the term "medicament" as used herein means any substance which provides a therapeutic and/or beneficial effect. The term "medicament" as used herein is not necessarily limited to substances which need Marketing Approval, but may include substances which can be used in cosmetics, nutraceuticals, food (including feeds and beverages for example), probiotic cultures, and natural remedies. In addition, the term "medicament" as used herein encompasses a product designed for incorporation in animal feed, for example livestock feed and/or pet food.

Pharmaceuticals

The composition of the present invention may be used as—or in the preparation of—a pharmaceutical. Here, the term "pharmaceutical" is used in a broad sense—and covers pharmaceuticals for humans as well as pharmaceuticals for animals (i.e. veterinary applications). In a preferred aspect, the pharmaceutical is for human use and/or for animal husbandry. The pharmaceutical can be for therapeutic purposes—which may be curative or palliative or preventative in nature. The pharmaceutical may even be for diagnostic purposes.

A pharmaceutically acceptable support may be for example a support in the form of compressed tablets, tablets, capsules, ointments, suppositories or drinkable solutions. Other suitable forms are provided below.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient. The pharmaceutical may be in the form of a solution or as a solid—depending on the use and/or the mode of application and/or the mode of administration.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof. The forms may also include gelatin capsules; fibre capsules, fibre tablets etc.; or even fibre beverages. Further examples of form include creams. For some aspects the microorganism used in the present invention may be used in pharmaceutical and/or cosmetic creams such as sun creams and/or after-sun creams for example.

Combinations with Prebiotics

The composition of the present invention may additionally contain one or more prebiotics. Prebiotics are a category of functional food, defined as non-digestible food ingredients that beneficially affect the host by selectively stimulating the growth and/or activity of one or a limited number of bacteria in the colon, and thus improve host health. Typically, prebiotics are carbohydrates (such as oligosaccharides), but the definition does not preclude non-carbohydrates. The most prevalent forms of prebiotics are nutritionally classed as soluble fibre. To some extent, many forms of dietary fibre exhibit some level of prebiotic effect.

In one embodiment, a prebiotic is a selectively fermented ingredient that allows specific changes, both in the composition and/or activity in the gastrointestinal microflora that confers benefits upon host well-being and health.

Suitably, the prebiotic may be used according to the present invention in an amount of 0.01 to 100 g/day, preferably 0.1 to 50 g/day, more preferably 0.5 to 20 g/day. In one embodiment, the prebiotic may be used according to the present invention in an amount of 1 to 100 g/day, preferably 2 to 9 g/day, more preferably 3 to 8 g/day. In another embodiment, the prebiotic may be used according to the present invention in an amount of 5 to 50 g/day, preferably 10 to 25 g/day.

Examples of dietary sources of prebiotics include soybeans, inulin sources (such as Jerusalem artichoke, jicama, and chicory root), raw oats, unrefined wheat, unrefined barley and yacon. Examples of suitable prebiotics include alginate, xanthan, pectin, locust bean gum (LBG), inulin, guar gum, galacto-oligosaccharide (GOS), fructo-oligosaccharide (FOS), polydextrose (i.e. Litesse®), lactitol, lactosucrose, soybean oligosaccharides, isomaltulose (Palatinose.™.), isomalto-oligosaccharides, gluco-oligosaccharides, xylo-oligosaccharides, manno-oligosaccharides, beta-glucans, cellobiose, raffinose, gentiobiose, melibiose, xylobiose, cyclodextrins, isomaltose, trehalose, stachyose, panose, pullulan, verbascose, galactomannans, and all forms of resistant starches. A particularly preferred example of a prebiotic is polydextrose.

In some embodiments, a combination of the *B. pseudocatenulatum* strain of the present invention and prebiotics according to the present invention exhibits a synergistic effect in certain applications (i.e. an effect which is greater than the additive effect of the bacteria when used separately).

EXAMPLES

Recent evidence indicates that the dysbiosis of the gut microbiome plays a pivotal role in human diseases such as obesity and diabetes (1, 2). Specific members of the gut microbiota with a causative contribution to disease/health phenotypes can serve not only as a powerful tool for disease diagnosis (3, 4) but also as targets for disease alleviation/treatment through various methods such as drugs (5), fecal microbiota transplantation (6) and diet (7). However, due to the complexity and the inter-individual variation of the gut microbiota itself and its interactions with the host and diet (8), the precision manipulation of the gut microbiota for achieving the optimum human health needs a more rigorous understanding at the genomic and molecular levels.

In one of our previous dietary intervention studies, we found that a diet enriched in non-digestible but fermentable carbohydrates, which was composed of whole grains, traditional Chinese medicinal foods and prebiotics (the WTP diet), not only significantly changed the gut microbiota but also improved the bioclinical parameters and inflammatory conditions in genetically obese children with Prader-Willi Syndrome (9). One particular beneficial bacterium, *B. pseudocatenulatum* was significantly enriched after the intervention, negatively correlated with other potential detrimental species and positively related to the improvement of the host clinical parameters (9).

One child from that cohort finished the intervention over 105 days. His bioclinical parameters were improved, with an over 25.8 kg initial bodyweight loss, together with a significant shift of the gut microbial community such as increases of *Faecalibacterium, Lactobacillus* and *Bifidobacterium* spp. Moreover, we found that *B. pseudocatenulatum* was the most dominant species in *Bifidobacterium* after the intervention. Intriguingly, we had isolated five strains from his fecal sample on Day 105 (10) and these strains had differential responses to the carbohydrate-enriched interventions. To understand the genetic traits involved in the bacterial niche adaption in the gut ecosystem and the interactions with the host and diet (11), we performed comparative genomics on *B. pseudocatenulatum*.

Results and Discussion

Improved bioclinical parameters and shifted gut microbiota

Figure 7:
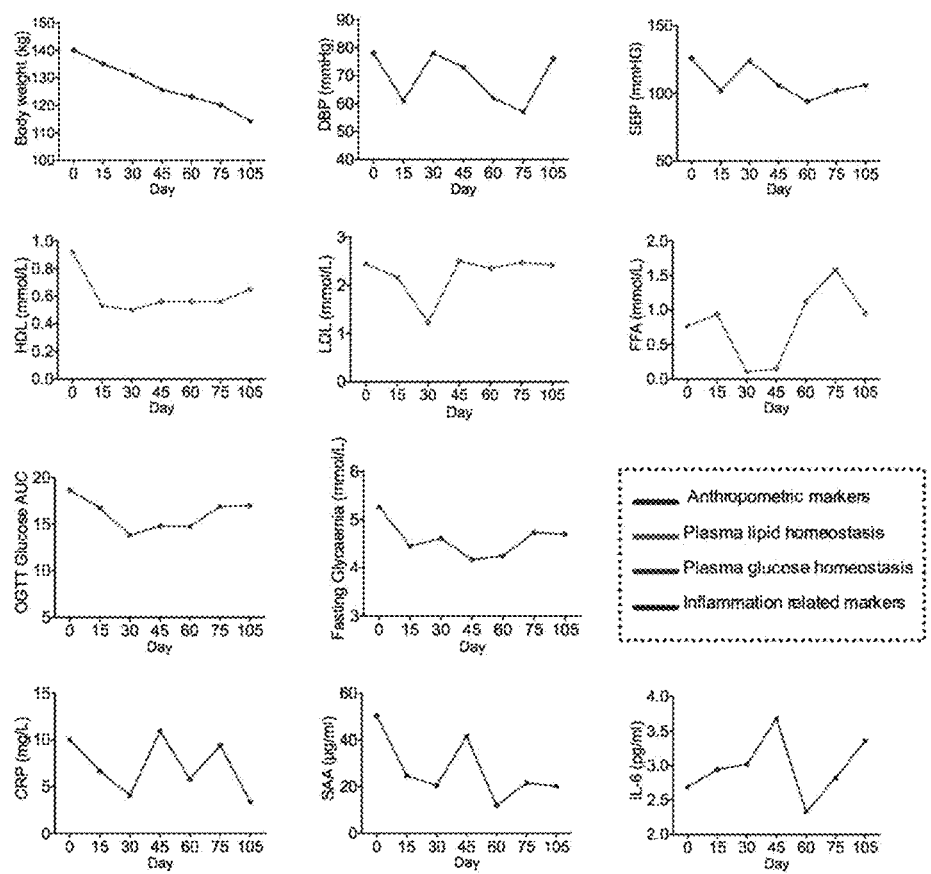
FIG. 7 The bioclincial parameters changed during the intervention. (red) Anthropometric markers. (green) Plasma lipid homeostasis. (blue) Plasma glucose homeostasis. (purple) Inflammation related markers. SAA: serum amyloid A protein; CRP: C-reactive protein.

The bioclinical variables of the obese child were improved during the intervention (FIG. 1 and FIG. 7). The weight was reduced from 140.1 kg to 114.3 kg and both the plasma glucose and lipid homeostasis were improved to the normal range. Two systemic inflammation markers, C-reactive protein (CRP) and serum amyloid A protein (SAA), were decreased after the intervention. The adiponectin increased from 2.17 µg/ml to 5.39 µg/ml and the leptin decreased from 63.82 ng/ml to 34.47 ng/ml, indicating an alleviation of the "at-risk" phenotype (12). In addition, lipopolysaccharide-binding protein (LBP), a surrogate marker for the bacterial antigen load in the blood (13), was decreased.

We obtained 25.2±4.8 million (mean±s.d.) high-quality paired-end reads per fecal sample at 7 time points (0, 15, 30, 45, 60, 75 and 105 days) via metagenomic sequencing. The composition of the gut microbiota shifted during the intervention (FIG. 2A) and showed different patterns responding to the three interventional phases (phase I: basic intervention from Day 0 to Day 60, phase II: basic intervention+100 g more Formula No. 3 from Day 60 to Day 75, phase III: reduced Formula No. 1+100 g more Formula No. 3 from Day 75 to Day 105, see methods for details). The defecation frequency of the obese child in the different phases was similar (on average, 3 to 4 times per day), and no diarrhea occurred. The diversity of the community was decreased during the intervention, which is consistent with the changes of the cohort (9). At the baseline, *Ruminococcus* and *Blautia* were the two most abundant genera, accounting for 26.95% and 18.41%, respectively. Meanwhile, *Bacteroides* and *Prevotella* were at a low abundance, suggesting that the community may belong to enterotype 3 (14). After the intervention, *Ruminococcus* and *Blautia* were reduced to low abundance, while *Bacteroides* and *Prevotella* were almost unaffected by the intervention. Compared with the baseline, *Faecalibacterium*, which was reported to be an anti-inflammatory species (15, 16) and a beneficial (5) commensal bacterium, increased in the phase I, with its abundance reaching 41.95% at Day 15. The sharp increase in *Faecalibacterium* might contribute to the alleviation of the inflammation in the first 15 days, as the CRP and SAA decreased by 33.37% and 50.85%, respectively, during this period. *Faecalibacterium* decreased to a low abundance in the phase II and III, when more oligosaccharides were provided. On the other hand, *Lactobacillus*, which is well equipped to metabolize oligosaccharides (17), had a low abundance at the baseline and during phase I, but became one of the most dominant genera starting from phase II. Several studies have reported the beneficial effects of *Lactobacillus* strains on the insulin resistance (18, 19). The dramatic increase of *Lactobacillus* may have contributed to the improvement of the insulin sensitivity from phase II as indicated by the remarkable decrease of the OGTT insulin AUC (area under the curve) and steady the OGTT glucose AUC during this period. The abundance of *Bifidobacterium*, which have the ability to metabolize a variety of carbohydrates via intra- and extracellular ways (20), was remarkable from Day 15 and remained a predominant genus through the entire intervention period: increasing from 27.47% when the child received the basic intervention, to 65.53% by Day 75, then decreasing to 36.41% when less of Formula No. 1 containing complex dietary fibers was provided. These results show that the *Bifidobacterium* population responds to the shifts in carbohydrate resources provided in the three phases, and in each phase, it occupied a superior ecological niche. Given the known beneficial effects of *Bifidobacterium* strains on obesity (21, 22), their essential role in the interaction network of our previous cohort study (9) and their sustained high abundance during the intervention, we speculate that they might have contributed to the continual decrease of body weight, BMI, waist circumference and hip circumference. Hence, we performed a deeper analysis on this genus.

Figure 8:
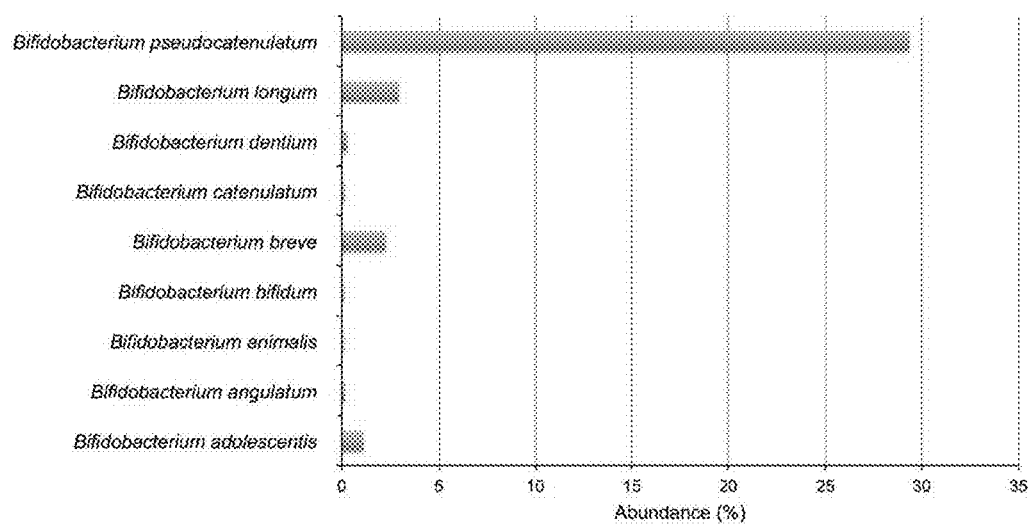
FIG. 8 The abundance of the 9 identified *Bifidobacterium* species in the gut microbial community on Day 105.
Figure 10:
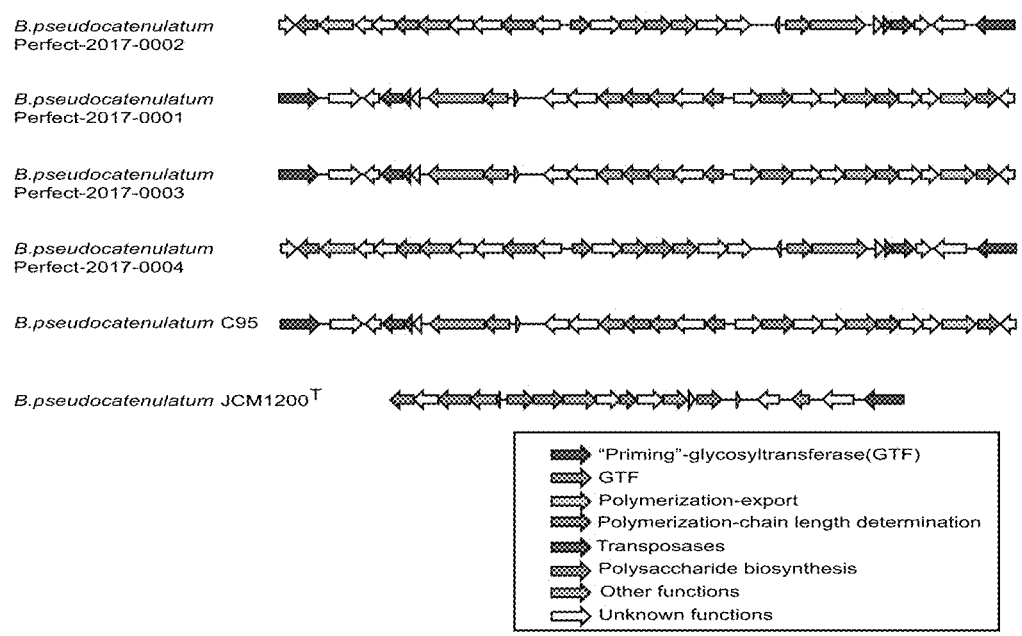
FIG. 10 Physical maps of the predicted eps clusters from the six complete *B. pseudocatenulatum*. The genes were showed as colored arrows according to their potential functions.
Figure 11:
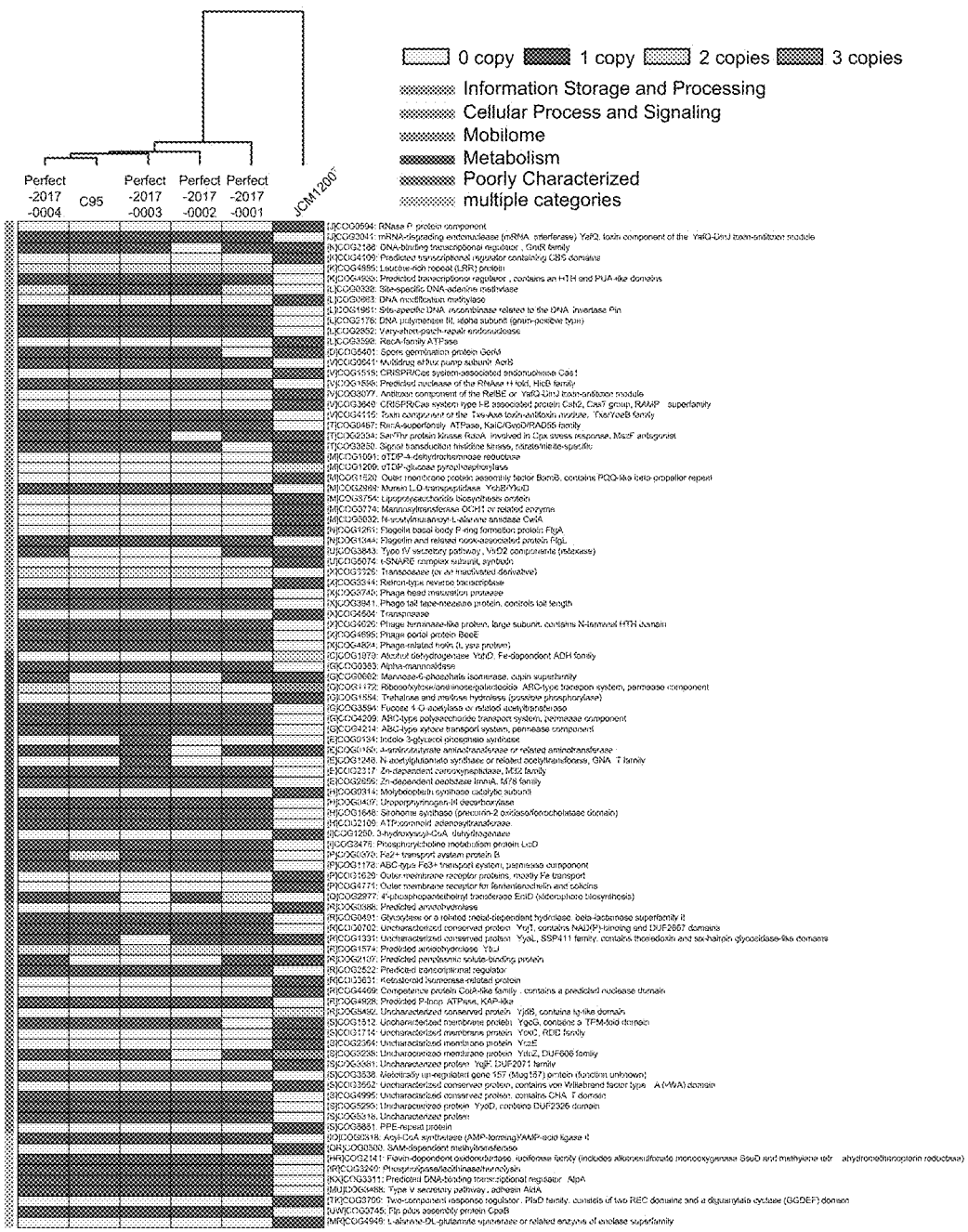
FIG. 11 Distribution of dispensable and unique COGs in the six *B. pseudocatenulatum* genomes. The heatmap shows the copy number of genes annotated as the particular COG function. The strains are clustered with Jaccard distance and Ward linkage method.

In total, nine *Bifidobacterium* species were identified in the post-intervention samples (FIG. 8). Among them, *B. pseudocatenulatum* was the most dominant, with an abundance of 29.36% in the whole gut microbiota on Day 105. *B. longum, B. breve* and *B. adolescentis* represented 9.94%, 7.61% and 3.75%, respectively, and the other five species had abundances lower than 1%.

Figure 2:
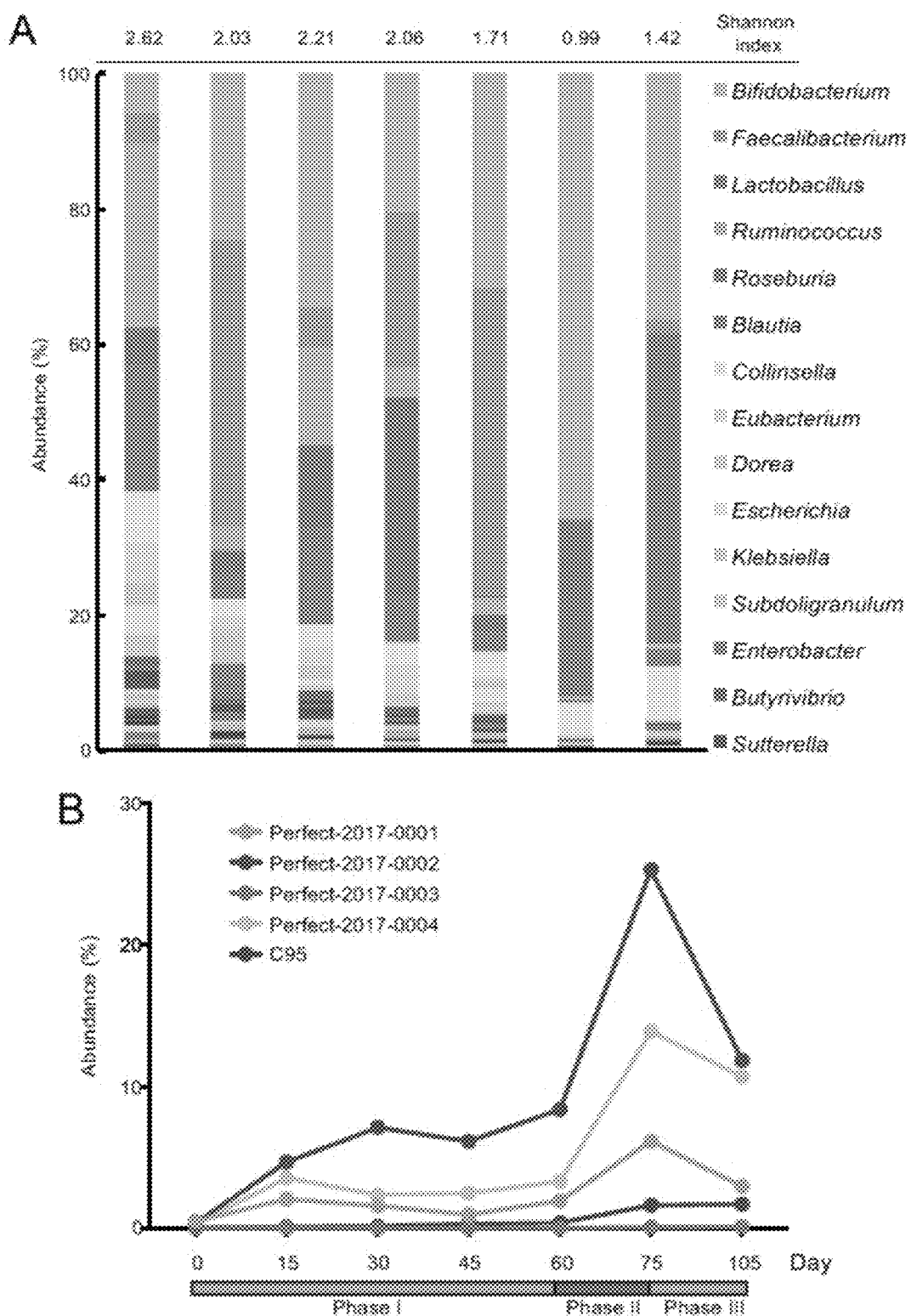
FIG. 2 shows shifts of the gut microbiota during the dietary intervention. (A) Genus-level gut microbiota compositions at the 7 time points. The top panel shows the Shannon index value and the bottom panel shows the percentage of each genus. According to the average abundance, the top 15 genera are labeled with their taxonomic names (B) The Differential abundances of the 5 *B. pseudocatenulatum* strains. Phase I: Day 0 to Day 60, basic dietary intervention; Phase II: Day 60 to Day 75, basic intervention+ 100 g more Formula No. 3; Phase III: less Formula No. 1+100 g more Formula No. 3)

Differential responses of the *B. pseudocatenulatum* strains to the intervention For a detailed study of the *B. pseudocatenulatum* population, we isolated and completely sequenced five *B. pseudocatenulatum* strains (hereafter defined as strains PERFECT-2017-0001, PERFECT-2017-0002, PERFECT-2017-0003, PERFECT-2017-0004 and C95 (23)) from the fecal sample collected from our subject on Day 105 (10). The abundance changes of these five strains at each time point were identified with Sigma (24) by aligning the metagenomic data with the complete genomes (FIG. 2B). Before the intervention, all of the strains had low abundances (maximum=0.5%, *B. pseudocatenulatum* PERFECT-2017-0001). The abundances of *B. pseudocatenulatum* PERFECT-2017-0003 and *B. pseudocatenulatum* C95 seemed unresponsive to the dietary interventions, as the former remained low abundance throughout the trial and the latter showed a small increase only during phase II and III. In contrast, the *B. pseudocatenulatum* PERFECT-2017-0001, *B. pseudocatenulatum* PERFECT-2017-0004 and *B. pseudocatenulatum* PERFECT-2017-0002 strains were responsive to the dietary interventions, Their abundance changes were consistent with those observed for the *Bifidobacterium* genus, suggesting these *B. pseudocatenulatum* strains primarily account for these changes. Indeed, after the intervention, these three strains had increased significantly, especially *B. pseudocatenulatum* PERFECT-2017-0002.

Figure 3:
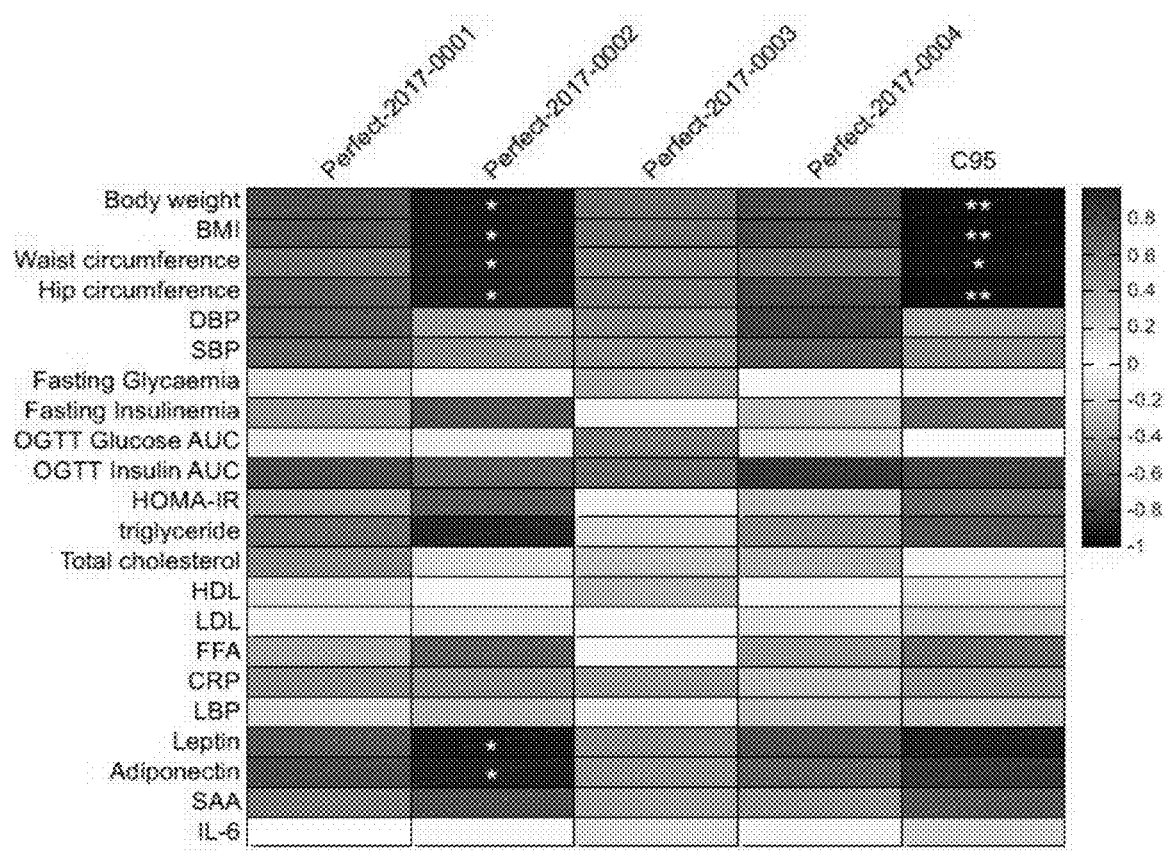
FIG. 3 shows correlations between the changes of clinical parameters with the abundance of the five *B. pseudocatenulatum* strains. Spearman correlation was performed. * Adjusted P<0.05; ** Adjusted P<0.01 (Benjamini & Hochberg 1995).

Consistent with the finding in the previous study (9), the improvements of the bioclinical variables were correlated with the increase in the *B. pseudocatenulatum* strains (FIG. 3). *B. pseudocatenulatum* C95 was negatively correlated to anthropometric markers, including body weight, BMI, waist circumference and hip circumference. Furthermore, *B. pseudocatenulatum* PERFECT-2017-0002 was also correlated to the improvement of inflammatory markers, including the decrease of leptin and the increase of adiponectin.

Pan-genome analysis of *B. pseudocatenulatum*

Based on our five complete *B. pseudocatenulatum* genomes and the available public data, including 5 draft *B. pseudocatenulatum* genomes and the complete genome of *B. pseudocatenulatum* JCM1200$^T$(25), a total of eleven *B. pseudocatenulatum* genomes were included in the pan-genome analysis. The pan-genome curve sho The bioclinical variables PERFECT-2017-0001 wed an asymptotic trend with an average growing rate of 100 genes per genome in the first six iterations and then decreased to a much smaller rate (FIG. 9A). The curve finally arrived at 2,482 genes. This shows that the further incorporation of additional genomes would lead to only a minor increase in the pan-genome size. The core-genome curve showed a more evidently asymptotic trend and a clear decrease in the first six iterations (FIG. 9B). The curve finally arrived at 1,427 genes. The pan-genome and core-genome trends suggest that *B. pseudocatenulatum* displayed a closed pan-genome, and six genomes are almost sufficient to describe the gene properties of *B. pseudocatenulatum*. Based on these results and to avoid the illegibility caused by draft genomes, we only used the six complete genomes in our subsequent analysis to explore the genomic features of *B. pseudocatenulatum*.

General Features of *B. pseudocatenulatum*

The genomes of our five strains and the *B. pseudocatenulatum* JCM1200$^T$ displayed an average of 2,355,185 bp and 56.63 G+C %, which is consistent with the G+C % range of the *Bifidobacterium* genus (26). Five or six rRNA operon loci were identified in the genomes of *B. pseudocatenulatum*, and in each genome, there was one additional copy of the 5S rRNA gene (Table 1). In addition, the heterogeneity across the 16S rRNA genes existed in all the genomes except for that of *B. pseudocatenulatum* JCM1200$^T$ (Table S1). On average, 54 tRNA genes were harbored in each *B. pseudocatenulatum* genome.

TABLE 1

General features of six complete complete genomes of *Bifidobacterium pseudocatenulatum*

| FEATURE | Perfect-2017-0002 | Perfect-2017-0001 | Perfect-2017-0003 | Perfect-2017-0004 | C95 | JCM1200$^T$ |
|---|---|---|---|---|---|---|
| Genome length (bp) | 2341029 | 2380612 | 2352149 | 2393824 | 2349745 | 2313752 |
| Number of genes | 1854 | 1883 | 1913 | 1895 | 1868 | 1817 |
| tRNA | 55 | 54 | 54 | 54 | 54 | 55 |
| 16S rRNA | 6 | 5 | 6 | 5 | 5 | 6 |
| 23S rRNA | 6 | 5 | 6 | 5 | 5 | 6 |
| 5S rRNA | 7 | 6 | 7 | 6 | 6 | 7 |
| Hypothetical proteins | 372 | 381 | 366 | 380 | 363 | 372 |
| Hypothetical proteins (%) | 20 | 20 | 19 | 20 | 19 | 20 |
| Gene with assigned function (%) | 80 | 80 | 81 | 80 | 81 | 80 |
| GC(%) | 56.59 | 56.76 | 56.65 | 56.78 | 56.63 | 56.38 |
| CAZy | 106 | 104 | 104 | 106 | 106 | 111 |

TABLE S1

The heterogeneity of 16S rRNA gene

*B. pseudocatenulatum* Perfect-2017-0001

|  | Copy1 | Copy2 | Copy3 | Copy4 | Copy5 |
|---|---|---|---|---|---|
| Copy1 | 100 | 100 | 100 | 100 | 99.9 |
| Copy2 | 100 | 100 | 100 | 100 | 99.9 |
| Copy3 | 100 | 100 | 100 | 100 | 99.9 |
| Copy4 | 100 | 100 | 100 | 100 | 99.9 |
| Copy5 | 99.9 | 99.9 | 99.9 | 99.9 | 100 |

*B. pseudocatenulatum* Perfect-2017-0002

|  | Copy1 | Copy2 | Copy3 | Copy4 | Copy5 | Copy6 |
|---|---|---|---|---|---|---|
| Copy1 | 100 | 100 | 100 | 99.9 | 100 | 99.7 |
| Copy2 | 100 | 100 | 100 | 99.9 | 100 | 99.7 |
| Copy3 | 100 | 100 | 100 | 99.9 | 100 | 99.7 |
| Copy4 | 99.9 | 99.9 | 99.9 | 100 | 99.9 | 99.6 |
| Copy5 | 100 | 100 | 100 | 99.9 | 100 | 99.7 |
| Copy6 | 99.7 | 99.7 | 99.7 | 99.6 | 99.7 | 100 |

*B. pseudocatenulatum* Perfect-2017-0003

|  | Copy1 | Copy2 | Copy3 | Copy4 | Copy5 | Copy6 |
|---|---|---|---|---|---|---|
| Copy1 | 100 | 100 | 100 | 100 | 100 | 99.9 |
| Copy2 | 100 | 100 | 100 | 100 | 100 | 99.9 |
| Copy3 | 100 | 100 | 100 | 100 | 100 | 99.9 |
| Copy4 | 100 | 100 | 100 | 100 | 100 | 99.9 |
| Copy5 | 100 | 100 | 100 | 100 | 100 | 99.9 |
| Copy6 | 99.9 | 99.9 | 99.9 | 99.9 | 99.9 | 100 |

*B. pseudocatenulatum* Perfect-2017-0004

|  | Copy1 | Copy2 | Copy3 | Copy4 | Copy5 |
|---|---|---|---|---|---|
| Copy1 | 100 | 100 | 99.9 | 100 | 100 |
| Copy2 | 100 | 100 | 99.9 | 100 | 100 |
| Copy3 | 99.9 | 99.9 | 100 | 99.9 | 99.9 |
| Copy4 | 100 | 100 | 99.9 | 100 | 100 |
| Copy5 | 100 | 100 | 99.9 | 100 | 100 |

TABLE S1-continued

The heterogeneity of 16S rRNA gene

B. pseudocatenulatum C95

|       | Copy1 | Copy2 | Copy3 | Copy4 | Copy5 |
|-------|-------|-------|-------|-------|-------|
| Copy1 | 100   | 99.9  | 100   | 100   | 100   |
| Copy2 | 99.9  | 100   | 99.9  | 99.9  | 99.9  |
| Copy3 | 100   | 99.9  | 100   | 100   | 100   |
| Copy4 | 100   | 99.9  | 100   | 100   | 100   |
| Copy5 | 100   | 99.9  | 100   | 100   | 100   |

B. pseudocatenulatum JCM1200$^T$

|       | Copy1 | Copy2 | Copy3 | Copy4 | Copy5 | Copy6 |
|-------|-------|-------|-------|-------|-------|-------|
| Copy1 | 100   | 100   | 100   | 100   | 100   | 100   |
| Copy2 | 100   | 100   | 100   | 100   | 100   | 100   |
| Copy3 | 100   | 100   | 100   | 100   | 100   | 100   |
| Copy4 | 100   | 100   | 100   | 100   | 100   | 100   |
| Copy5 | 100   | 100   | 100   | 100   | 100   | 100   |
| Copy6 | 100   | 100   | 100   | 100   | 100   | 100   |

Figure 4:
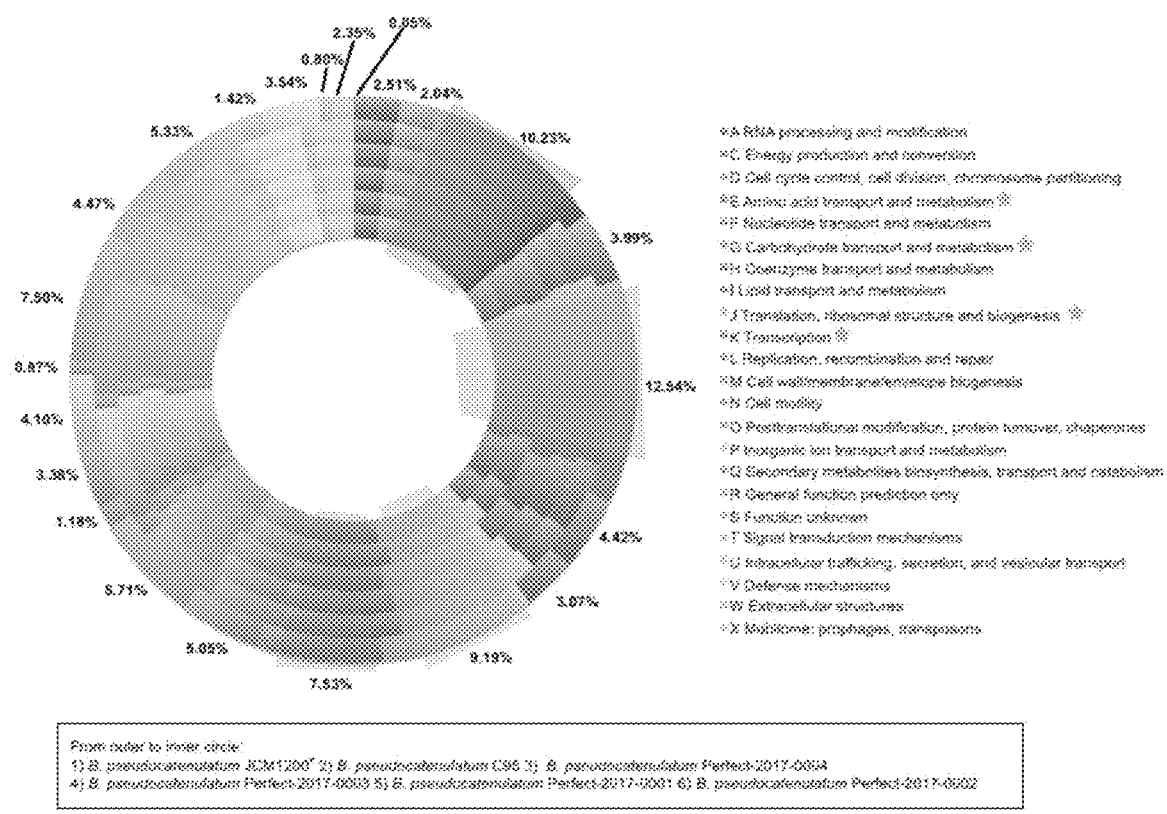
FIG. 4 shows the cluster of Orthologues (COG) classification of the orthologous genes of *B. pseudocatenulatum*. For each COG the average percentage among the six complete *B. pseudocatenulatum* genomes has been indicated.

An average of 1,871 Open Reading Frames (ORFs) per genomes was predicted, with 80% of the detected ORFs were functionally assigned via in silico prediction based on BLAST against the NCBI nr database, and the remaining 20% were predicted as hypothetical proteins (Table 1). The identification of orthologous genes according to the COG (Cluster of Orthologous Groups) (27) showed that the majority of the genes in the genome of B. pseudocatenulatum were involved in various housekeeping functions especially those for carbohydrate transport and metabolism (12.54%) as well as amino acid transport and metabolism (10.23%) (FIG. 4). These percentages were in agreement with those of other Bifidobacterium genomes (28, 29).

Based on the genomic analysis and supported by experimental evidence, several host colonization factors of Bifidobacteria have already been identified including functions involved in bile resistance and adhesins (11). Resistance to bile is important for the colonization of many intestinal bacteria, as bile acids can have antimicrobial activity at physiological concentrations (30). Bile salt hydrolase and/or bile acid transporter, which confer bile resistance, were identified in all the six B. pseudocatenulatum strains. In the aspect of adhesion, all of the genomes harbored genes encoding for enolase, and DnaK, which has been shown to be plasminogen-binding related proteins in B. animalis subsp. lactis BI07(31, 32). Moreover, the genes encoding for transaldolase, which is involved in the mucin binding found in four B. bifidum strains (33) and von Willebrand factor A, which has been reported to promote adhesion to extracellular matrices (34), existed in each genome as well. The existence of these functional genes suggests that, similar to other Bifidobacterium species, B. pseudocatenulatum has the genomic basis to colonize in the human intestine.

Genomic Microdiversity of B. pseudocatenulatum

The average nucleotide identity (ANI) among the six complete B. pseudocatenulatum genomes met the threshold for species demarcation (35), as the minimum value was 97.76%. A slightly higher similarity within the strains isolated from the same habitat (B. pseudocatenulatum PERFECT-2017-0001, PERFECT-2017-0002, PERFECT-2017-0003, PERFECT-2017-0004 and C95, minimum ANI=99.88%) was observed when compared them with B. pseudocatenulatum JCM1200$^T$ (the maximum ANI=97.80%), which was isolated from a different habitat. These results indicated the high degree of synteny across all these genomes, which is confirmed by the dot-plot alignments for the genomes (FIG. 5A), although less colinearity and some differences (including indels) were apparent in the dot-plots between B. pseudocatenulatum JCM1200$^T$ and the other five strains. A notable example of this variation was the eps gene cluster, which encodes for exopolysaccharides (EPS). The EPS can form a slime layer that is attached to the cell and also can be released into the environment (36). Some EPSs produced by Bifidobacterium were considered to potentially contribute several beneficial activities to their hosts, including the modulation of the immune system, antagonism against pathogens, functions as scavenging agents and modulation of the microbial community (37). One copy of the eps gene cluster was identified in each complete genome of B. pseudocatenulatum (FIG. S4) and these eps clusters were identical in our five B. pseudocatenulatum strains, but quite different to that found in B. pseudocatenulatum JCM1200$^T$.

Figure 5:
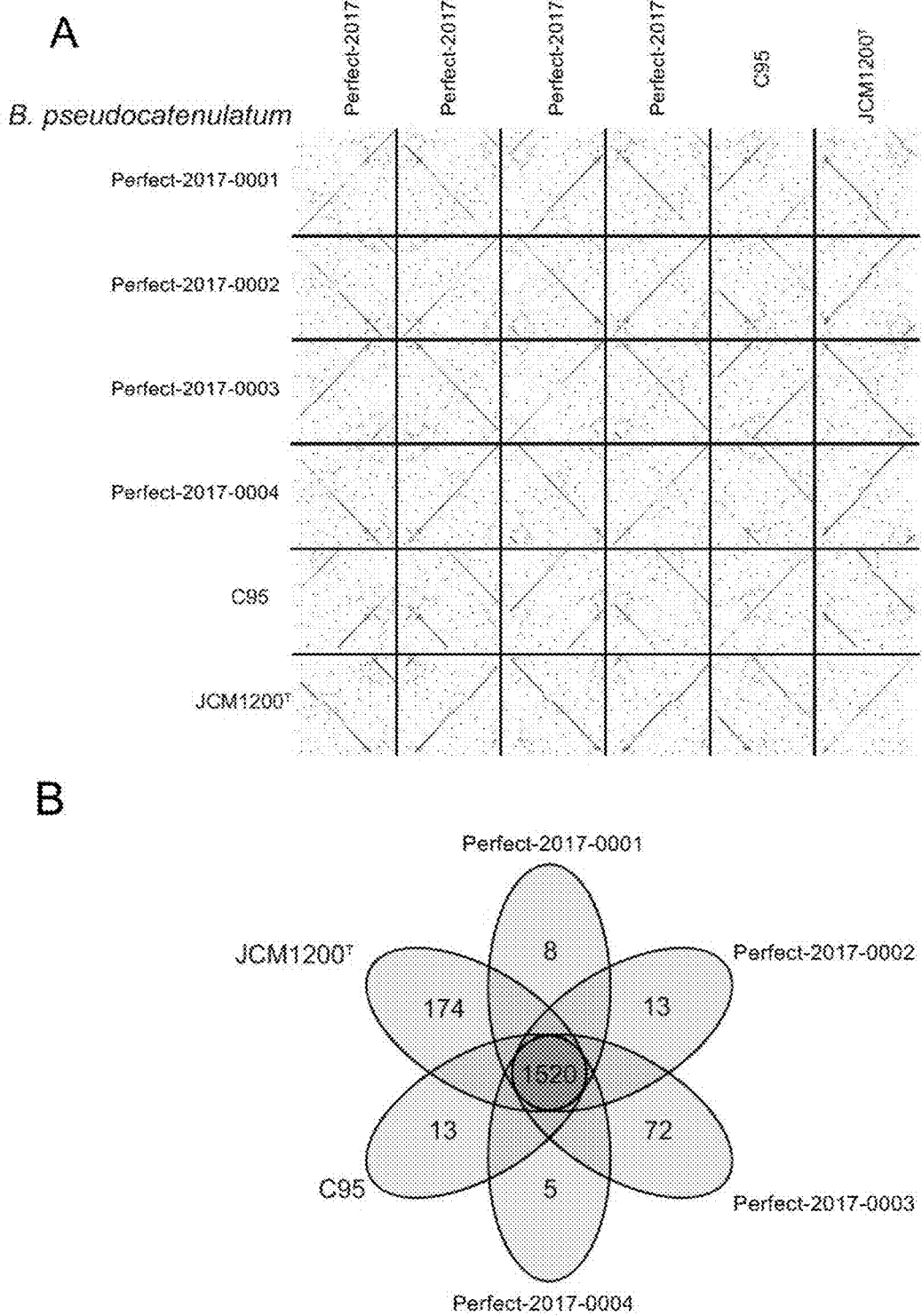
FIG. 5 shows the genomic variations among the *B. pseudocatenulatum* strains (A) Pair-wise dot plot comparisons based on genomic sequences alignment with MUMmer among the six complete *B. pseudocatenulatum* genomes (B) The Venn diagram shows the number of core and unique gene groups in each strain.

All ORFs identified on the six complete genomes were compared with BLASTP and further clustered with the MCL algorithm, which revealed the presence of 2,115 gene groups (FIG. 5B). Of these ~72% (1,520) were shared by all six B. pseudocatenulatum genomes, which represent the core genome of B. pseudocatenulatum. A total of 312 dispensable gene groups, which were present only in a subset of the examined B. pseudocatenulatum genomes, were identified. Over 61.48% of the unique groups were specific to B. pseudocatenulatum JCM1200T. Similar results were obtained based on COG assignments, with 1,101 COG families identified from the six complete B. pseudocatenulatum genomes. Of these 59 COG families were only present in a subset of the examined B. pseudocatenulatum genomes, and 37 additional COGs were unique to a single strain, with 35 of these identified only in B. pseudocatenulatum JCM1200$^T$ (FIG. S5). There were also 46 COG families that were found in our isolates, but were absent from the B. pseudocatenulatum JCM1200$^T$ genome. Interestingly, at least some of these differences relate to the mobilome and DNA rearrangement, with our isolates possessing more unique COGs related to prophage functions, cellular processes and signaling, while the B. pseudocatenulatum JCM1200$^T$ possessing more unique COGs include those involved with the CRISPR/Cas system(s).

Particularly, our isolates and B. pseudocatenulatum JCM1200$^T$ were exposed to distinct carbohydrate resources. The former were originated from the fecal sample of the post-intervention child, who received mixed materials from whole grains and TCM food plants that are rich in dietary fiber and powders including fructo-oligosaccharides and oligoisomaltoses, while the latter was isolated from feces of an infant, who was speculated to receive relatively simpler carbohydrates. Correspondingly, genetic variations involved in carbohydrate transport and metabolism were found, such as the B. pseudocatenulatum JCM1200$^T$ lacked COG0383 (alpha-mannosidase), COG3594 (fucose 4-O-acetylase or related acetyltransferase), COG4209 (ABC-type polysaccharide transport system, permease component) and COG4214 (ABC-type xylose transport system, permease component) but uniquely had COG1554 (Trehalose and maltose hydrolase (possible phosphorylase)).

Figure 6:
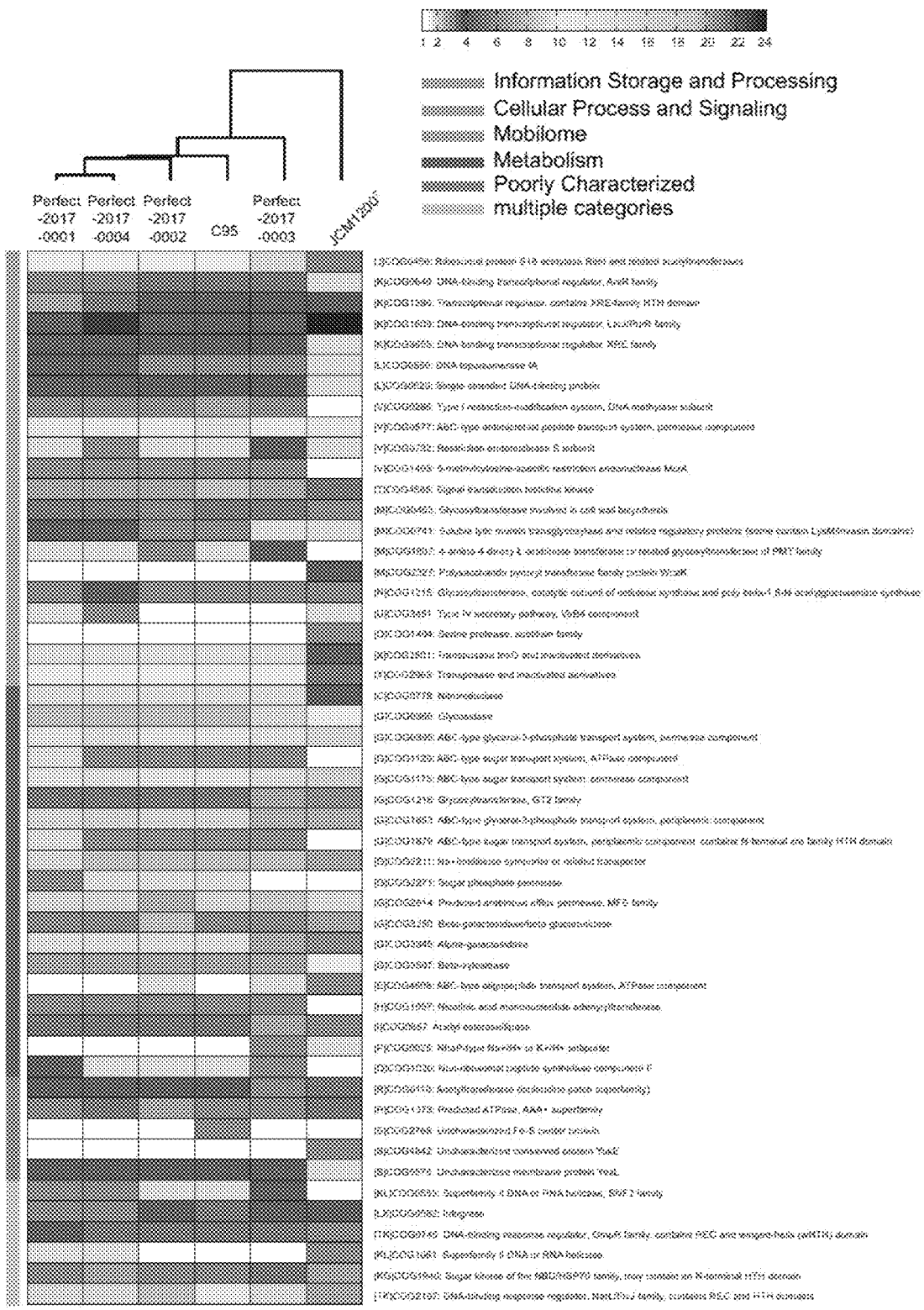
FIG. 6 Distribution of core COGs having a disparity in copy number with at least 2 copies. The heatmap shows the copy number of genes annotated as the particular COG function. The strains are clustered with the Euclidean distance and the Ward linkage method.

The different copy numbers of the core COGs contributed to the microdiversity of B. pseudocatenulatum as well. Among the 1,005 core COGs that appeared in each complete B. pseudocatenulatum genome, 51 COGs involved in various functional categories had a disparity in the copy number with at least 2 copies (FIG. 6). According to the distribution of these COGs, B. pseudocatenulatum JCM1200$^T$ was the most different compared to our 5 strains.

Previous studies have reported the microdiversity of different strains in the same species originating from the same habitat (38-40). Among our five *B. pseudocatenulatum* strains, the differences appeared to result from variations in the copy number of genes assigned to specific core COG families, instead of differences in terms of the presence/absence of unique and/or dispensable COGs. The clustering result (FIG. 6) was consistent with the differential responses of the strains to the carbohydrate interventions. In that context, *B. pseudocatenulatum* C95 and *B. pseudocatenulatum* PERFECT-2017-0003, which were almost unaffected by the intervention, were clearly separated from the three responsive strains; with both *B. pseudocatenulatum* PERFECT-2017-0001 and *B. pseudocatenulatum* PERFECT-2017-0004, which had moderate responses to the intervention grouped together; and *B. pseudocatenulatum* PERFECT-2017-0002, the strain most responsive to the intervention, further separable from the other 4 strains, but most similar to *B. pseudocatenulatum* PERFECT-2017-0001 and *B. pseudocatenulatum* PERFECT-2017-0004.

With the respect to the carbohydrate transport and metabolism, *B. pseudocatenulatum* PERFECT-2017-0002 had the highest copy number of COG2814 (predicted arabinose efflux permease, MFS family) and COG3250 (beta-galactosidase/beta-glucuronidase). Moreover, among the 5 strains, 106±2 (mean±s.d.) ORFs were identified as carbohydrate-active enzymes (CAZy) genes, which accounted for 41 CAZy families The *B. pseudocatenulatum* PERFECT-2017-0002 genome harbored all of the identified CAZy families and had the greatest copy number of these genes. It also harbored the highest copy number of genes encoding for carbohydrate esterases, which are reported to deacetylate plant polysaccharides to overcome the complexity and cooperate with glycoside hydrolases in plant polysaccharide degradation (41). These features are presumed to be the principal differences accounting for the responsiveness of *B. pseudocatenulatum* PERFECT-2017-0002 to the dietary intervention, whereby it accounts for more than 50% of the total *B. pseudocatenulatum*, and a substantial proportion of the entire Bifidobacterial population throughout the intervention.

Conclusion

In a previous study investigating how the WTP diet results in weight loss in genetically obese persons, *B. pseudocatenulatum* was identified as the most abundant *Bifidobacterium* species. Here, we show that specific strains of *B. pseudocatenulatum* show variations in their response to the dietary intervention and we use comparative genomics to identify possible reasons underlying these dynamics. The five *B. pseudocatenulatum* strains isolated as part of this study showed some differences relative to *B. psedocatenulatum* JCM1200$^T$ isolated from an infant feces, which indicates the effect of different environmental parameters on genome microdiversity (42). Much of the observed microdiversity among our five isolates are the variations of the copy numbers of core COG families and these differences provide a plausible explanation for the variations in the populations of the five strains during the intervention. In particular, *B. pseudocatenulatum* PERFECT-2017-0002, which genetically had the more diverse and greater copy numbers of genes for plant polysaccharides, had the greatest abundance in response to the dietary intervention. The coexistence and distribution of multiple strains is intuitive because it would support the survival of the population as a whole over a broader range of environmental conditions than would be possible for a homogeneic population (43). Thus the co-existence of the five strains with diverse responses to the dietary intervention may work as a mechanism to ensure the stability and restoration of important beneficial species such as *B. pseudcatenulatum* in human gut. Importantly though, the five *B. pseudocatenulatum* strains identified in this study were also found to have different correlations with host bioclinical parameters, suggesting that at least some of the beneficial functions ascribed to changes in the gut microbiota are strain-specific (44). More studies of the type presented here will be necessary to ensure that the full potential of the health benefits sought from dietary manipulations of the gut microbiota are realized.

Materials and Methods

Clinical Investigation

The study was performed under the approval of the Ethics Committee of the School of Life Sciences and Biotechnology, Shanghai Jiao Tong University (No. 2012-2016). The clinical trial was registered at Chinese Clinical Trial Registry (No. ChiCTR-ONC-12002646). Written informed consent was obtained from the guardians of the obese child.

In GuangDong Women and Children Hospital, Guanzhou, Chian, the obese child received a hospitalized dietary intervention for 105 days. The volunteer did not take any exercise program. A diet based on whole grains, traditional Chinese medicinal foods, and prebiotics (WTP diet) (7) (The three ready-to-consume pre-prepared foods, Formula No. 1, Formula No. 2 and Formula No. 3 in the diet were manufactured by PERFECT (CHINA) CO., LTD) was administered in combination with appropriate amounts of vegetables, fruits and nuts according to dietician's advice. The intervention was divided into three phases. In the phase I (Day 0 to Day 60), the child received the basic intervention (9). In the phase II (Day 60 to Day 75), he consumed 100 g more Formula No. 3. During the Phase III (Day 75 to Day 105), he still consumed 100 g more Formula No. 3 but less Formula No. 1 was provided.

Biological samples, anthropometric data and clinical laboratory analysis were obtained at the 7 time points (0, 15, 30, 45, 60, 75, and 105 day). The measurements of the bioclinical parameters were as same as our previous study (9).

Metagenomic Sequencing and Analysis

DNA extraction from fecal samples for metagenomic sequencing was conducted as previously described (45). Seven samples were sequenced using Illumina Hiseq 2000 platform at Shanghai Genergy Bio-technology Co., Ltd. DNA library preparation followed Illumina's instructions. Cluster generation, template hybridization, isothermal amplification, linearization, blocking, and denaturing and hybridization of the sequencing primers were performed according to the workflow indicated by the provider. Libraries were constructed followed by high-throughput sequencing to obtain paired-end reads with 151 bp in the forward and reverse directions.

Flexbar (46) was used to trim the adapter from the reads. Prinseq (47) was employed a) to trim the reads from the 3' end until reaching the first nucleotide with a quality threshold of 20; b) to remove read pairs if either read was shorter than 75 bp or contained 'N' bases, and c) to de-duplicate the reads. Reads that could be aligned to the human genome (H. sapiens, UCSC hg19) were removed (aligned with Bowtie2 (48), using -reorder -no-hd -no-contain -dovetail). On average, 25.3±4.1 million (mean±s.d.) paired-end reads for each sample were retained and used for further analysis.

MetaPhlan (49) (-bt2_ps very-sensitive-local) was used to calculate the abundance of *Bifidobacterium* species at Day 105. Sigma was used to calculate the abundance of our five *B. pseudocatenulatum* strains (24).

Whole Genome Sequencing and Data Assembly

The genomes of *B. pseudocatenulatum* PERFECT-2017-0001, *B. pseudocatenulatum* PERFECT-2017-0002, *B. pseudocatenulatum* PERFECT-2017-0003, *B. pseudocatenulatum* PERFECT-2017-0004, and *B. pseudocatenulatum* C95 were sequenced by PacBio RS II sequencing instrument with approximately 245-, 415-, 285-, 459- and 198-fold coverage, respectively (Nextomics Biosciences, Wuhan 430000, China). HGAP/Quiver (50) was used to de novo assemble the subreads, followed by miniums2 (51) and Quiver. Each strain was assembled into one contig, which corresponding to its chromosome.

General Features Prediction

Open Reading Frame (ORF) prediction was performed by the combination of Prodigal v2_60 (52) and BLAST alignment. The identified ORFs were then annotated using BLASTP against the NCBI nr database. Ribosomal RNA genes were detected using Rnammer v1.2 (53) and transfer RNA genes were identified with tRNAscan-SE v.14 (54). The identity matrix between all 16S rRNA gene was calculated with USEARCH v8.0.1517 (55). The assignment of COGs was done with COGtriangles (ftp://ftp.ncbi.nih.gov/pub/wolf/COGs/COGsoft/).

Pan-Genome Calculation

PGAPv1.12 (56) was used to calculate the pan-genome of *B. pseudocatenulatum*. Functional gene clustering was performed by GF (Gene Family) method and the pan-genome profile was build then.

Genomic Comparison

Software package MUMmer v3.0 (57) was used to perform the whole genome sequence alignments at the nucleotide level. For each genome pair, the average nucleotide identity (ANI) was calculated using the program JSpecies version 1.2.1 (35). At protein level, sequences were compared in all against all way using BLASTP (maximum E-value 1e-10, minimum alignment identity 50% and minimum alignment coverage 50% for either protein) and then clustering into gene families using Markov Cluster Algorithm (MCL) implement in PGAP v1.12.

The identification of Exopolysaccharide (EPS) gene cluster

In silico analysis of Bifido-eps cluster was performed by searching the putative priming-GTF (p-gtf) gene: rfbP (NP_695444) and cpsD (NP_695447) in each genome (37) followed by manually checking the genes surrounding the p-gtf.

The Identification of Carbohydrate Activate Enzymes (CAZys)

A local-version database of dbCAN v3.0 (58) was downloaded. Genes in each genome were aligned to the database using HMMscan (59). The alignment was parsed with hmmscan-parser.sh provided by dbCAN and the best-hit was retained.

Availability of Data and Materials

All the genomes generated in this study and the metagenomic dataset has been deposited in the European Nucleotide Archive (ENA) (www.ebi.ac.uk/ena) under the accession number PRJEB18557. All the other genomes of *B. pseudocatenulatum* used for our analysis were downloaded from NCBI database with the following accession number: AP012330.1, CDPW00000000.1, ABXX02000001, JEOD01000001, JGZF01000001 and *B. pseudocatenulatum* D2CA was download from MetaHIT (http://www.sanger.ac.uk/resources/downloads/bacteria/metahit/).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCE CITED

1. Zhao L. 2013. The gut microbiota and obesity: from correlation to causality. Nat Rev Microbiol 11:639-647.
2. Boulange C L, Neves A L, Chilloux J, Nicholson J K, Dumas M E. 2016. Impact of the gut microbiota on inflammation, obesity, and metabolic disease. Genome Med 8:42.
3. Qin N, Yang F, Li A, Prifti E, Chen Y, Shao L, Guo J, Le Chatelier E, Yao J, Wu L, Zhou J, Ni S, Liu L, Pons N, Batto J M, Kennedy S P, Leonard P, Yuan C, Ding W, Chen Y, Hu X, Zheng B, Qian G, Xu W, Ehrlich S D, Zheng S, Li L. 2014. Alterations of the human gut microbiome in liver cirrhosis. Nature 513:59-64.
4. Zhang X, Zhang D, Jia H, Feng Q, Wang D, Liang D, Wu X, Li J, Tang L, Li Y, Lan Z, Chen B, Li Y, Zhong H, Xie H, Jie Z, Chen W, Tang S, Xu X, Wang X, Cai X, Liu S, Xia Y, Li J, Qiao X, Al-Aama J Y, Chen H, Wang L, Wu Q J, Zhang F, Zheng W, Li Y, Zhang M, Luo G, Xue W, Xiao L, Li J, Chen W, Xu X, Yin Y, Yang H, Wang J, Kristiansen K, Liu L, Li T, Huang Q, Li Y, Wang J. 2015. The oral and gut microbiomes are perturbed in rheumatoid arthritis and partly normalized after treatment. Nat Med 21:895-905.
5. Xu J, Lian F, Zhao L, Zhao Y, Chen X, Zhang X, Guo Y, Zhang C, Zhou Q, Xue Z, Pang X, Zhao L, Tong X. 2015. Structural modulation of gut microbiota during alleviation of type 2 diabetes with a Chinese herbal formula. ISME J 9:552-562.
6. Kelly C R, Kahn S, Kashyap P, Laine L, Rubin D, Atreja A, Moore T, Wu G. 2015. Update on Fecal Microbiota Transplantation 2015: Indications, Methodologies, Mechanisms, and Outlook. Gastroenterology 149:223-237.
7. Xiao S, Fei N, Pang X, Shen J, Wang L, Zhang B, Zhang M, Zhang X, Zhang C, Li M, Sun L, Xue Z, Wang J, Feng J, Yan F, Zhao N, Liu J, Long W, Zhao L. 2014. A gut microbiota-targeted dietary intervention for amelioration of chronic inflammation underlying metabolic syndrome. FEMS Microbiol Ecol 87:357-367.
8. Human Microbiome Project C. 2012. Structure, function and diversity of the healthy human microbiome. Nature 486:207-214.
9. Zhang C, Yin A, Li H, Wang R, Wu G, Shen J, Zhang M, Wang L, Hou Y, Ouyang H, Zhang Y, Zheng Y, Wang J, Lv X, Wang Y, Zhang F, Zeng B, Li W, Yan F, Zhao Y, Pang X, Zhang X, Fu H, Chen F, Zhao N, Hamaker B R, Bridgewater L C, Weinkove D, Clement K, Dore J, Holmes E, Xiao H, Zhao G, Yang S, Bork P, Nicholson J K, Wei H, Tang H, Zhang X, Zhao L. 2015. Dietary Modulation of Gut Microbiota Contributes to Alleviation of Both Genetic and Simple Obesity in Children. EBioMedicine 2:966-982.
10. Wu H, Wang R, Zhao Y, Pang X, Shen J, Zhang C. 2015. Exploring Carbohydrate Utilization Capacity of *Bifidobacterium pseudocate-*

11. nulatum Isolated from a Morbidly Obese Child after Dietary Intervention. Genomics and Applied Biology 34:1384-1391.
12. Grimm V, Westermann C, Riedel C U. 2014. Bifidobacteria-host interactions—an update on colonisation factors. Biomed Res Int 2014:960826.
13. Labruna G, Pasanisi F, Nardelli C, Caso R, Vitale D F, Contaldo F, Sacchetti L. 2011. High leptin/adiponectin ratio and serum triglycerides are associated with an "at-risk" phenotype in young severely obese patients. Obesity (Silver Spring) 19:1492-1496.
14. Zweigner J, Schumann R R, Weber J R. 2006. The role of lipopolysaccharide-binding protein in modulating the innate immune response. Microbes Infect 8:946-952.
15. Arumugam M, Raes J, Pelletier E, Le Paslier D, Yamada T, Mende D R, Fernandes G R, Tap J, Bruls T, Batto J M, Bertalan M, Borruel N, Casellas F, Fernandez L, Gautier L, Hansen T, Hattori M, Hayashi T, Kleerebezem M, Kurokawa K, Leclerc M, Levenez F, Manichanh C, Nielsen H B, Nielsen T, Pons N, Poulain J, Qin J, Sicheritz-Ponten T, Tims S, Torrents D, Ugarte E, Zoetendal E G, Wang J, Guarner F, Pedersen O, de Vos W M, Brunak S, Dore J, Meta HITC, Antolin M, Artiguenave F, Blottiere H M, Almeida M, Brechot C, Cara C, Chervaux C, Cultrone A, Delorme C, Denariaz G, et al. 2011. Enterotypes of the human gut microbiome. Nature 473:174-180.
16. Fujimoto T, Imaeda H, Takahashi K, Kasumi E, Bamba S, Fujiyama Y, Andoh A. 2013. Decreased abundance of *Faecalibacterium prausnitzii* in the gut microbiota of Crohn's disease. J Gastroenterol Hepatol 28:613-619.
17. Sokol H, Pigneur B, Watterlot L, Lakhdari O, Bermudez-Humaran L G, Gratadoux J J, Blugeon S, Bridonneau C, Furet J P, Corthier G, Grangette C, Vasquez N, Pochart P, Trugnan G, Thomas G, Blottiere H M, Dore J, Marteau P, Seksik P, Langella P. 2008. *Faecalibacterium prausnitzii* is an anti-inflammatory commensal bacterium identified by gut microbiota analysis of Crohn disease patients. Proc Natl Acad Sci USA 105:16731-16736.
18. Ganzle M G, Follador R. 2012. Metabolism of oligosaccharides and starch in *lactobacilli*: a review. Front Microbiol 3:340.
19. Andreasen A S, Larsen N, Pedersen-Skovsgaard T, Berg R M, Moller K, Svendsen K D, Jakobsen M, Pedersen B K. 2010. Effects of *Lactobacillus acidophilus* NCFM on insulin sensitivity and the systemic inflammatory response in human subjects. Br J Nutr 104:1831-1838.
20. Hulston C J, Churnside A A, Venables M C. 2015. Probiotic supplementation prevents high-fat, overfeeding-induced insulin resistance in human subjects. Br J Nutr 113:596-602.
21. Charbonneau M R, Blanton L V, DiGiulio D B, Reiman D A, Lebrilla C B, Mills D A, Gordon J I. 2016. A microbial perspective of human developmental biology. Nature 535:48-55.
22. Wang J, Tang H, Zhang C, Zhao Y, Derrien M, Rocher E, van-Hylckama Vlieg J E, Strissel K, Zhao L, Obin M, Shen J. 2015. Modulation of gut microbiota during probiotic-mediated attenuation of metabolic syndrome in high fat diet-fed mice. ISME J 9:1-15.
23. Stenman L K, Waget A, Garret C, Klopp P, Burcelin R, Lahtinen S. 2014. Potential probiotic *Bifidobacterium animalis* ssp. *lactis* 420 prevents weight gain and glucose intolerance in diet-induced obese mice. Benef Microbes 5:437-445.
24. STALEY J, KRIEG N. 1984. Classification of prokaryotes organisms: an overview. KRIEG, N R, HOLT, J G Bergey's manual of systemayic bacteriology 1.
25. Ahn T H, Chai J, Pan C. 2015. Sigma: strain-level inference of genomes from metagenomic analysis for biosurveillance. Bioinformatics 31:170-177.
26. Morita H, Toh H, Oshima K, Nakano A, Arakawa K, Takayama Y, Kurokawa R, Takanashi K, Honda K, Hattori M. 2015. Complete genome sequence of *Bifidobacterium pseudocatenulatum* JCM 1200(T) isolated from infant feces. J Biotechnol 210:68-69.
27. Bottacini F, Medini D, Pavesi A, Turroni F, Foroni E, Riley D, Giubellini V, Tettelin H, van Sinderen D, Ventura M. 2010. Comparative genomics of the genus *Bifidobacterium*. Microbiology 156:3243-3254.
28. Galperin M Y, Makarova K S, Wolf Y I, Koonin E V. 2015. Expanded microbial genome coverage and improved protein family annotation in the COG database. Nucleic Acids Res 43:D261-269.
29. Bottacini F, O'Connell Motherway M, Kuczynski J, O'Connell K J, Serafini F, Duranti S, Milani C, Turroni F, Lugli G A, Zomer A, Zhurina D, Riedel C, Ventura M, van Sinderen D. 2014. Comparative genomics of the *Bifidobacterium breve* taxon. BMC Genomics 15:170.
30. O'Callaghan A, Bottacini F, O'Connell Motherway M, van Sinderen D. 2015. Pangenome analysis of *Bifidobacterium longum* and site-directed mutagenesis through by-pass of restriction-modification systems. BMC Genomics 16:832.
31. Begley M, Gahan C G M, Hill C. 2005. The interaction between bacteria and bile. Fems Microbiology Reviews 29:625-651.
32. Candela M, Biagi E, Centanni M, Turroni S, Vici M, Musiani F, Vitali B, Bergmann S, Hammerschmidt S, Brigidi P. 2009. Bifidobacterial enolase, a cell surface receptor for human plasminogen involved in the interaction with the host. Microbiology 155:3294-3303.
33. Candela M, Centanni M, Fiori J, Biagi E, Turroni S, Orrico C, Bergmann S, Hammerschmidt S, Brigidi P. 2010. DnaK from *Bifidobacterium animalis* subsp. *lactis* is a surface-exposed human plasminogen receptor upregulated in response to bile salts. Microbiology 156:1609-1618.
34. Gonzalez-Rodriguez I, Sanchez B, Ruiz L, Turroni F, Ventura M, Ruas-Madiedo P, Gueimonde M, Margolles A. 2012. Role of extracellular transaldolase from *Bifidobacterium bifidum* in mucin adhesion and aggregation. Appl Environ Microbiol 78:3992-3998.
35. Pareti F I, Fujimura Y, Dent J A, Holland L Z, Zimmerman T S, Ruggeri Z M. 1986. Isolation and characterization of a collagen binding domain in human von Willebrand factor. J Biol Chem 261:15310-15315.
36. Richter M, Rossello-Mora R. 2009. Shifting the genomic gold standard for the prokaryotic species definition. Proc Natl Acad Sci USA 106:19126-19131.
37. Schmid J, Sieber V, Rehm B. 2015. Bacterial exopolysaccharides: biosynthesis pathways and engineering strategies. Front Microbiol 6:496.
38. Hidalgo-Cantabrana C, Sanchez B, Milani C, Ventura M, Margolles A, Ruas-Madiedo P. 2014. Genomic overview and biological functions of exopolysaccharide biosynthesis in *Bifidobacterium* spp. Appl Environ Microbiol 80:9-18.
39. Zhang X L, Gao P P, Chao Q F, Wang L H, Senior E, Zhao L P. 2004. Microdiversity of phenol hydroxylase genes among phenol-degrading isolates of *Alcaligenes* sp from an activated sludge system. Fems Microbiology Letters 237:369-375.
40. Mayo Y J, Zhang X J, Xia X, Zhong H H, Zhao L P. 2010. Versatile aromatic compound-degrading capacity and microdiversity of Thauera strains isolated from a coking wastewater treatment bioreactor. Journal of Industrial Microbiology & Biotechnology 37:927-934.
41. Patra R, Chattopadhyay S, De R, Ghosh P, Ganguly M, Chowdhury A, Ramamurthy T, Nair G B, Mukhopadhyay A K. 2012. Multiple Infection and Microdiversity among *Helicobacter pylori* Isolates in a Single Host in India. Plos One 7.
42. Biely P. 2012. Microbial carbohydrate esterases deacetylating plant polysaccharides. Biotechnol Adv 30:1575-1588.
43. Jezbera J, Jezberova J, Kasalicky V, Simek K, Hahn M W. 2013. Patterns of Limnohabitans microdiversity across a large set of freshwater habitats as revealed by Reverse Line Blot Hybridization. PLoS One 8:e58527.
44. Moore L R, Rocap G, Chisholm S W. 1998. Physiology and molecular phylogeny of coexisting *Prochlorococcus* ecotypes. Nature 393:464-467.
45. Zhang C, Zhao L. 2016. Strain-level dissection of the contribution of the gut microbiome to human metabolic disease. Genome Med 8:41.
46. Fei N, Zhao L. 2013. An opportunistic pathogen isolated from the gut of an obese human causes obesity in germfree mice. ISME J 7:880-884.
47. Dodt M, Roehr J T, Ahmed R, Dieterich C. 2012. FLEXBAR-Flexible Barcode and Adapter Processing for Next-Generation Sequencing Platforms. Biology (Basel) 1:895-905.
48. Schmieder R, Edwards R. 2011. Quality control and preprocessing of metagenomic datasets. Bioinformatics 27:863-864.
49. Langmead B, Salzberg S L. 2012. Fast gapped-read alignment with Bowtie 2. Nat Methods 9:357-359.
50. Segata N, Waldron L, Ballarini A, Narasimhan V, Jousson O, Huttenhower C. 2012. Metagenomic microbial community profiling using unique clade-specific marker genes. Nat Methods 9:811-814.
51. Chin C S, Alexander D H, Marks P, Klammer A A, Drake J, Heiner C, Clum A, Copeland A, Huddleston J, Eichler E E, Turner S W, Korlach J. 2013. Nonhybrid, finished microbial genome assemblies from long-read SMRT sequencing data. Nat Methods 10:563-569.
52. Sommer D D, Delcher A L, Salzberg S L, Pop M. 2007. Minimus: a fast, lightweight genome assembler. BMC Bioinformatics 8:64.
53. Hyatt D, Chen G L, Locascio P F, Land M L, Larimer F W, Hauser L J. 2010. Prodigal: prokaryotic gene recognition and translation initiation site identification. BMC Bioinformatics 11:119.
54. Lagesen K, Hallin P, Rodland E A, Staerfeldt H H, Rognes T, Ussery D W. 2007. RNAmmer: consistent and rapid annotation of ribosomal RNA genes. Nucleic Acids Res 35:3100-3108.
55. Lowe T M, Eddy S R. 1997. tRNAscan-SE: a program for improved detection of transfer RNA genes in genomic sequence. Nucleic Acids Res 25:955-964.
56. Edgar R C. 2010. Search and clustering orders of magnitude faster than BLAST. Bioinformatics 26:2460-2461.
57. Zhao Y, Wu J, Yang J, Sun S, Xiao J, Yu J. 2012. PGAP: pan-genomes analysis pipeline. Bioinformatics 28:416-418.
58. Kurtz S, Phillippy A, Delcher A L, Smoot M, Shumway M, Antonescu C, Salzberg S L. 2004. Versatile and open software for comparing large genomes. Genome Biol 5:R12.
59. Yin Y, Mayo X, Yang J, Chen X, Mayo F, Xu Y. 2012. dbCAN: a web resource for automated carbohydrate-active enzyme annotation. Nucleic Acids Res 40:W445-451.
60. Finn R D, Clements J, Eddy S R. 2011. HMMER web server: interactive sequence similarity searching. Nucleic Acids Res 39:W29-37.

What is claimed is:

1. A composition for administering to a subject in need thereof and effective to at least one of (i) at least one of prevent and treat at least one disease selected from the group consisting of overweight, obesity, hyperglycemia, diabetes, fatty liver, dyslipidemia, metabolic syndrome, infections in obese or overweight subjects, and adipocyte hypertrophy and diabetes, (ii) reduce simple or genetic obesity, alleviate metabolic deteriorations, or reduce inflammation and fat accumulation in the subject, and (iii) establish as a foundation species that defines a structure of a healthy gut ecosystem, renders a gut environment unfavorable to pathogenic and detrimental bacteria, and reduces a concentration of enterobacteria in intestinal content with respect to an untreated control, the composition comprising:
(1) a *Bifidobacterium pseudocatenulatem* strain selected from the group consisting of Perfect-2017-0001, with accession no. CGMCC 13650, Perfect-2017-0002, with accession no. CGMCC 13651, Perfect-2017-0003, with accession no. CGMCC 13653, Perfect-2017-0004, with accession no. CGMCC 13654,
(2) a *Lactobacillus mucosae* strain, and
(3) a pharmaceutically acceptable or dietary carrier,
wherein the pharmaceutically acceptable or dietary carrier is selected from the group consisting of alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, sweetening agents, flavoring agents, coloring agents, emulsifying agents, suspending agents, diluents, and glycerin.

2. The composition of claim 1, which comprises strain Perfect-2017-0001, with accession no. CGMCC 13650.

3. The composition of claim 1, which comprises strain Perfect-2017-0002, with accession no. CGMCC 13651.

4. The composition of claim 1, which comprises strain Perfect-2017-0003, with accession no. CGMCC 13653.

5. The composition of claim 1, wherein the composition is a pharmaceutical composition.

6. The composition of claim 1, wherein the composition is a nutritional supplement or a nutritive composition.

7. The composition of claim 1, wherein the composition comprises at least $10^3$ to $10^{14}$ colony forming units of the strain per gram or millimeter of the composition.

8. The composition of claim 1, wherein the composition comprises at least one of cell components, metabolites, and secreted molecules, of the strain.

9. A method for preparing a composition of claim 1, comprising formulating the *Bifidobacterium pseudocatenulatem* strain or a highly into the composition.

* * * * *